(12) United States Patent
Fukikoshi et al.

(10) Patent No.: US 10,342,915 B2
(45) Date of Patent: Jul. 9, 2019

(54) SENSOR PAD KIT FOR LEAK DETECTION SENSOR, LEAK DETECTION SYSTEM, AND CHEMICAL LIQUID INJECTION SYSTEM

(71) Applicant: Nemoto Kyorindo Co., Ltd., Tokyo (JP)

(72) Inventors: Yumiko Fukikoshi, Tokyo (JP); Shigeru Nemoto, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 160 days.

(21) Appl. No.: 15/129,390

(22) PCT Filed: Mar. 26, 2015

(86) PCT No.: PCT/JP2015/059493
§ 371 (c)(1),
(2) Date: Sep. 26, 2016

(87) PCT Pub. No.: WO2015/147217
PCT Pub. Date: Oct. 1, 2015

(65) Prior Publication Data
US 2017/0100534 A1 Apr. 13, 2017

(30) Foreign Application Priority Data
Mar. 27, 2014 (JP) .................. 2014-067240

(51) Int. Cl.
*A61M 5/14* (2006.01)
*A61M 5/00* (2006.01)
*A61M 5/145* (2006.01)
*A61M 5/158* (2006.01)
*A61M 5/168* (2006.01)

(52) U.S. Cl.
CPC .......... *A61M 5/007* (2013.01); *A61M 5/1456* (2013.01); *A61M 5/14546* (2013.01);
(Continued)

(58) Field of Classification Search
CPC ................ A61M 5/007; A61M 5/1456; A61M 5/14546; A61M 5/16836; A61M 5/158;
(Continued)

(56) References Cited

U.S. PATENT DOCUMENTS

| 6,487,428 | B1 | 11/2002 | Culver et al. |
| 7,826,890 | B1 | 11/2010 | Winchester, Jr. et al. |
| 2007/0225637 | A1* | 9/2007 | Ono ..................... A61B 5/4875 604/65 |

(Continued)

FOREIGN PATENT DOCUMENTS

| JP | 1991-116844 | 12/1991 |
| JP | U11991116844 | 12/1991 |
| JP | 2011-206407 A | 10/2011 |

(Continued)

OTHER PUBLICATIONS

Internatonal Preliminary Report on Patentability in International Application No. PCT/JP2015/059493, dated Sep. 27, 2016.
(Continued)

*Primary Examiner* — Rex R Holmes
(74) *Attorney, Agent, or Firm* — Knobbe, Martens Olson & Bear LLP

(57) ABSTRACT

A sensor pad kit includes a sensor pad (701) which is flexible, and one surface of which is adhesive, having a sensor holding portion (702*a*) to which a sensor device (550) is to be attached, and at least two extended portions (718) extending toward an outer side from the sensor holding portion (702*a*) in a plan view, a fixing member (775) which fixes the sensor device to the sensor holding portion, and a peelable film (771) which is stuck to an adhesive surface of the sensor pad.

18 Claims, 28 Drawing Sheets

(52) U.S. Cl.
CPC ........ *A61M 5/158* (2013.01); *A61M 5/16836* (2013.01); *A61M 2005/1588* (2013.01); *A61M 2205/15* (2013.01); *A61M 2205/18* (2013.01); *A61M 2205/3306* (2013.01); *A61M 2205/3584* (2013.01); *A61M 2205/502* (2013.01); *A61M 2205/52* (2013.01); *A61M 2209/086* (2013.01)

(58) Field of Classification Search
CPC .......... A61M 2205/18; A61M 2205/52; A61M 2205/3584; A61M 2209/086; A61M 2205/15; A61M 2205/502; A61M 2205/3306; A61M 2005/1588
See application file for complete search history.

(56) References Cited

U.S. PATENT DOCUMENTS

| | | | | |
|---|---|---|---|---|
| 2012/0071743 | A1* | 3/2012 | Todorov .............. | G06F 19/3481 600/372 |
| 2012/0215163 | A1* | 8/2012 | Hanson ............... | A61M 5/1413 604/67 |

FOREIGN PATENT DOCUMENTS

| | | | |
|---|---|---|---|
| JP | 2012-213417 A | 11/2012 | |
| WO | WO 2006/030764 A1 | 3/2006 | |

OTHER PUBLICATIONS

Notification of Reasons for Refusal in corresponding Japanese Application No. 2016-510510, dated Dec. 11, 2018.

\* cited by examiner

SENSOR PAD KIT FOR LEAK DETECTION SENSOR, LEAK DETECTION SYSTEM, AND CHEMICAL LIQUID INJECTION SYSTEM

TECHNICAL FIELD

The present invention relates to a sensor pad kit for leak detecting sensor, a leak detection system and a chemical liquid injection system. The present invention, in particular, relates to a sensor pad kit that can be attached stably to a portion of a patient's body, a leak detection system and a chemical liquid injection system.

BACKGROUND ART

Currently, as medical imaging diagnosis apparatuses such as CT (Computed Tomography) scanners, MRI (Magnetic Resonance Imaging) apparatuses, PET (Positron Emission Tomography) apparatuses have been known. While using such imaging apparatuses, a chemical liquid such as a contrast medium or a saline (hereinafter, simply referred to as 'a chemical liquid') is often injected into the patient's body.

While injecting the chemical liquid, sometimes a tip of an injection needle may come off a blood vessel of the patient and the chemical liquid is leaked out of the blood vessel (this is also called as 'extravascular leak'). In Patent Document 1 for example, a technology for determining if there is an extravascular leak or not has been disclosed. In the technology for determining the extravascular leak, infrared rays are irradiated to a portion of the patient's body by using a light-emitting diode (LED) and light reflected is received by a phototransistor. From the intensity of the light reflected, it is possible to determine if there is an extravascular leak or not.

PRIOR ART DOCUMENT

Patent Document

Patent Document 1: WO2006/030764

SUMMARY OF INVENTION

Technical Problem

Incidentally, in the abovementioned method for detecting leak, it is necessary to attach a leak detecting sensor to a surface of patient's body. It would be conceived that a fixing method for attaching such sensor device to patient's arm by a band for example can be adopted. However, such a fixing method is time-consuming. Moreover, the reliability of fixing may vary according to an operator.

Therefore, an object of the present invention is to provide a sensor pad kit for leak detecting sensor which can be attached to patient's body comparatively easily, and which enables to attach a sensor device to a portion of the patient's body stably, a leak detection system, and a chemical liquid injection system.

Means for Solving the Problems

A sensor pad kit according to an aspect of the present invention for solving the problem is as follows.
1. The sensor pad kit includes
a sensor pad which is flexible, and one surface of which is adhesive, having a sensor holding portion to which a sensor device is to be attached, and at least two extended portions extending toward an outer side from the sensor holding portion in a plan view,
a fixing member which fixes the sensor device to the sensor holding portion, and
a peelable film which is stuck to an adhesive surface of the sensor pad.

Description of Terminology

The 'chemical liquid' refers to a contrast medium, a saline, or a mixture of a contrast medium and a saline, or any other liquid formulation (such as an anticancer agent).

The 'sensor device', in the present specification, refers to a device that is to be used by attaching to a part of the patient's body, for example a device such as a sensor head for detecting leak.

Specific examples of contrast medium are a contrast medium having an iodine concentration of 240 mg/ml (for example, viscosity 3.3 Pa·s at 37° C. and specific gravity 1.268 to 1.296), a contrast medium having an iodine concentration of 300 mg/ml (for example, viscosity 6.1 mPa·s at 37° C. and specific gravity 1.335 to 1.371), a contrast medium having an iodine concentration of 350 mg/ml (for example, viscosity 10.6 mPa·s at 37° C. and specific gravity 1.392 to 1.433) and the like.

Specific example of saline is a saline in which, 20 mL of saline contains 180 mg of sodium chloride (for example, viscosity 0.9595 mPa·s at 20° C. and specific gravity 1.004 to 1.006).

The 'control section' may be a computer unit which includes components such as a CPU (Central Processing Unit) that carries out arithmetic processing (computation), a memory, an interface, and realizes various functions by executing computer programs stored in the memory. As an example, the computer unit may be a one-chip microcomputer including a CPU, a ROM (Read Only Memory), a RAM (Random Access Memory), and an I/F (Interface), in which, a computer program is mounted. Apart from this, the control section may be a section provided as an electric circuit.

'Connection'—In the present specification, in a case in which, a certain component is said to be connected to another component for example, it refers to two modes namely, a mode in which, the two components are connected directly, and a mode in which the two components are connected indirectly via one or a plurality of predetermined intermediate components. Moreover, a connection of components for transmitting an electric signal or for carrying out a predetermined data communication is not limited to a wired connection and may be a wireless connection.

Effects of the Invention

According to the present invention, it is possible to provide a sensor pad kit which can be attached to patient's body comparatively easily, and furthermore, after fixing, enables to fix stably a sensor device to a portion of the patient' body, a leak detection system, and a chemical liquid injection system.

DESCRIPTION OF EMBODIMENT

Figure 1:
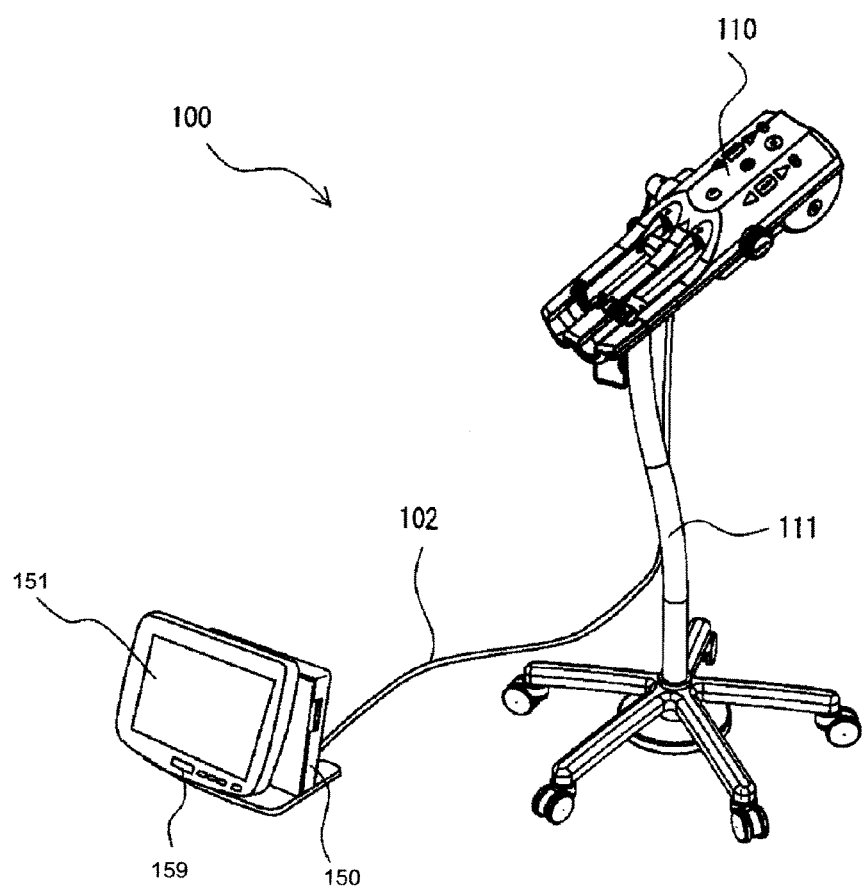
FIG. 1 is a perspective view showing an example of an arrangement of chemical liquid injection apparatus.

Technical matters of embodiments described below can be combined appropriately with other technical matters of other embodiments.

First Embodiment

A chemical liquid injection apparatus will be described below by referring to FIG. 1 to FIG. 3. A chemical liquid injection apparatus 100 according to an embodiment of the present invention includes an injection head 110 held at an upper portion of a movable stand 111, and a console 150 electrically connected to the injection head 110 by a cable 102. In this example, two syringes 200C and 200P are to be removably mounted side-by-side in parallel on the injection head 110.

In the following description, the syringes 200C and 200P may also be referred to as only 'the syringe 200' instead of distinguishing as syringes 200C and 200P. The 'injection head' will also be called as the injector or the injector head. Moreover, in the following description, although a certain specific aspect indicated in a diagram is described, various modifications of chemical liquid injection apparatuses and syringes other than those described below are possible. Modified example of the present invention will be described later.

[A1. Syringe]

Chemical liquids to be filled in the syringes 200C and 200P (refer to FIG. 2) include contrast media and saline. For example, one syringe 200C may be filled with a contrast media and the other syringe 200P may be filled with a saline.

The syringe 200 includes a cylinder member 221 having a hollow cylindrical shape, and a piston member 222 which is slidably inserted into the cylinder member 221. The cylinder member 221 may have a cylinder flange 221a formed at a proximal-end portion thereof, and a conduit-tube portion 221b formed at a distal-end portion thereof. By sliding down the piston member 222 into the cylinder member 221, a chemical liquid in the syringe is pushed outside via the conduit-tube portion 221b.

An extension tube 230 is connected to the conduit-tube portion 221b of each syringe 200. The extension tube 230 may be a so-called T-shaped tube or a Y-shaped tube, and may include a tube 231a extended up to a branched (bifurcated) portion from the conduit-tube portion 221b of one syringe 200C, a tube 231b extended up to a branched (bifurcated) portion from the conduit-tube portion 221b of the other syringe 200P, and a tube 231c extended from the branched portion toward a patient. An injection needle for example, is to be connected to a distal-end side (not shown) of the tube 231c. By puncturing the injection needle into a blood vessel of the patient and pushing out the chemical liquid inside the syringe 200C and/or the syringe 200P, the chemical liquid is injected into the blood vessel.

Figure 3:
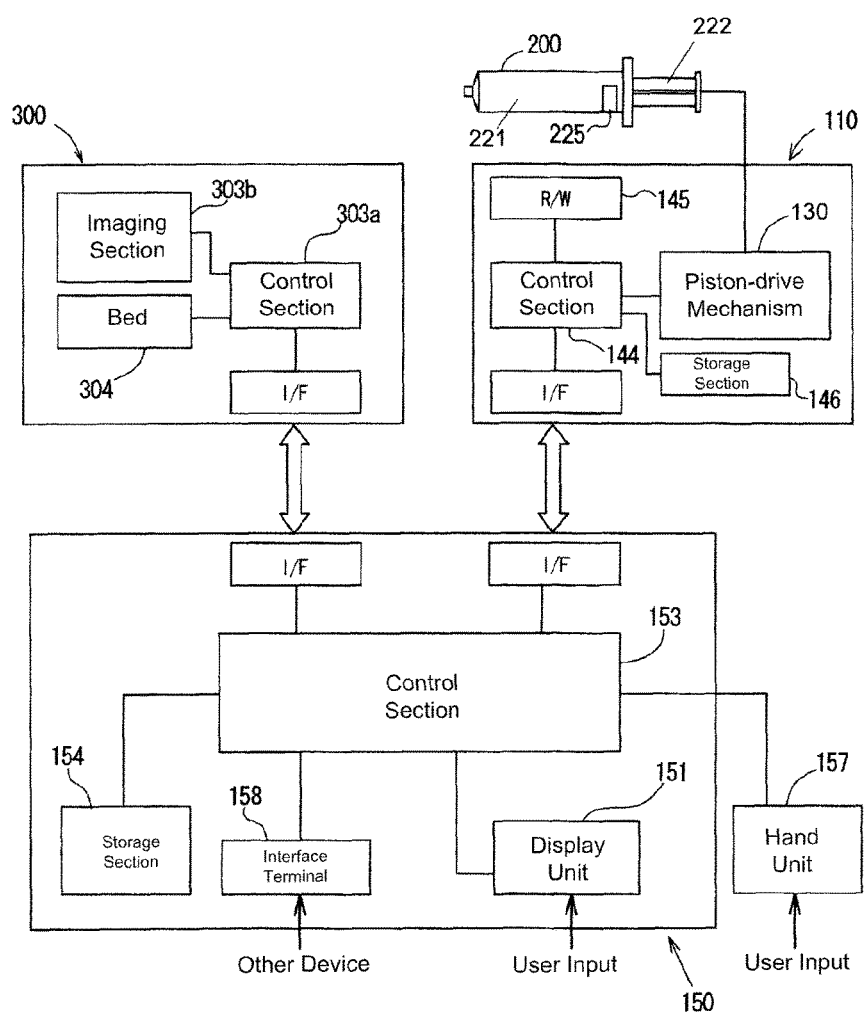
FIG. 3 is a block diagram of the chemical liquid injection apparatus and an imaging apparatus.

As shown in FIG. 3, an IC tag 225 may be put on a portion of the cylinder member 221. Information about the syringe (such as cylinder identification information, pressure that cylinder can withstand, inner diameter of the cylinder member, and stroke of the piston member), and information of the chemical liquid (name (product name for example) filled in the syringe, information of constituents such as iodine quantity, date of expiry, and content of the chemical liquid) has been stored in the IC tag 225. The IC tag may have a specific unique ID. The IC tag may include at least one information selected from syringe size, product serial number, and chemical-liquid standardization code. Tags such as an RFID (Radio frequency identification) tag can be used as the IC tag 225. A position where the IC tag 225 is to be attached may be on an outer peripheral surface of the cylinder member 221, and specifically near the cylinder flange on the outer peripheral surface.

The following changes may be made in an arrangement of syringe.

(a1) A connector portion that connects the extension tube and the saline syringe (for example, a connector portion to be connected to the saline syringe) has a function of a check valve.

Figure 4A:
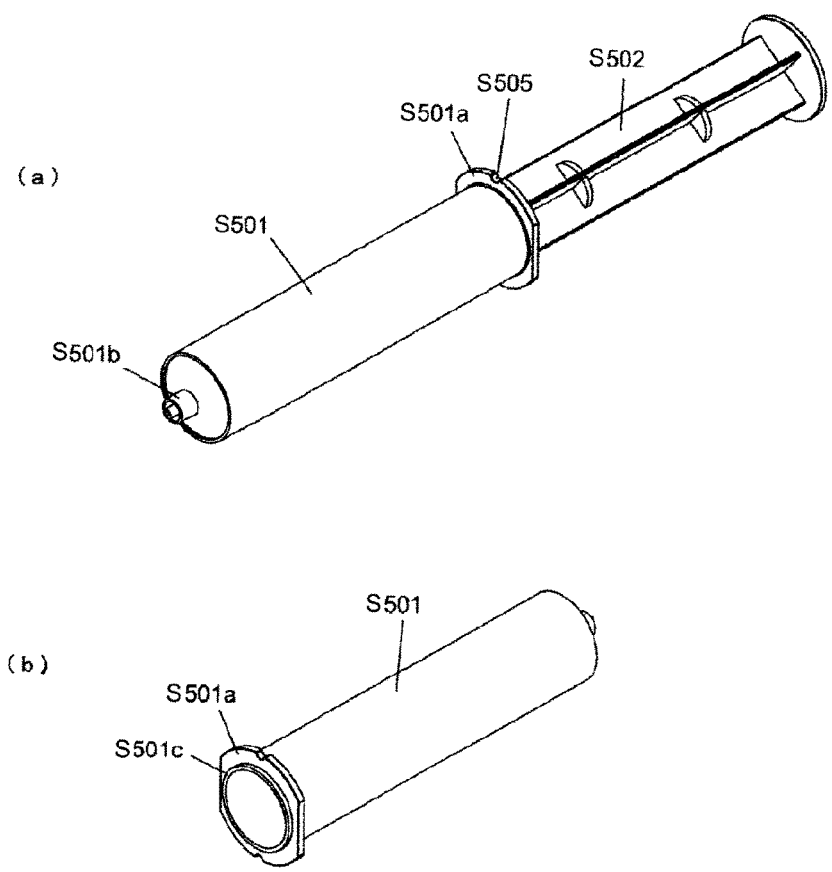
FIG. 4A is a perspective view showing a specific example of syringe.
Figure 4B:
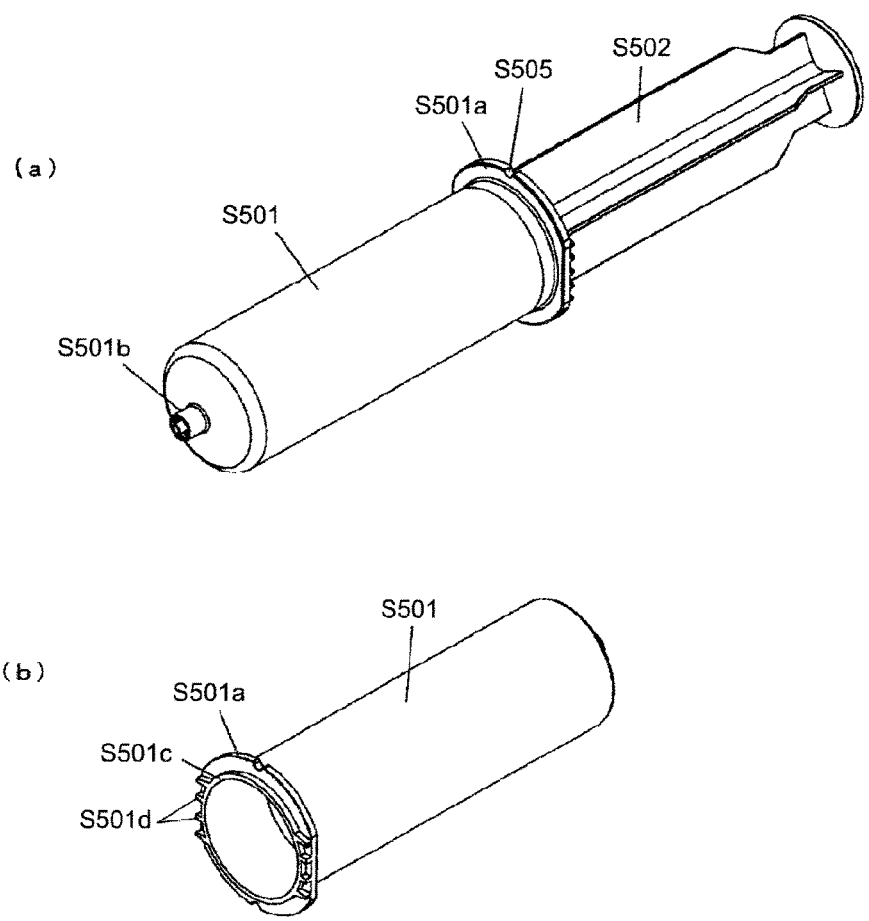
FIG. 4B is a perspective view showing another specific example of syringe.

(a2) The syringe may be a syringe specifically shown in FIG. 4A and FIG. 4B. The syringe in FIG. 4A is a syringe for 100 ml. The syringe includes a cylinder member S501 and a piston member S502. A cylinder flange S501a of the cylinder member S501 has an I-cut shape (a shape in which, two side of a circle are removed by a straight line). Two notches S505 are cut in an outer peripheral portion of the flange S501a (only one notch is shown). A conduit-tube portion 501b at a front end of the cylinder member S501 may be a portion for Luer-lock connection having two cylindrical portions on an inner side and an outer side disposed concentrically. As shown in FIG. 4A (b), a protruding portion S501c having a ring shape may be formed on a back surface of the cylinder flange S501a. Similarly, the other of the two syringes may be as shown in FIG. 4B, which is a syringe for 200 ml for example. This syringe, similarly as the abovementioned syringe, may include the cylinder member S501 and the piston member 502, and the cylinder flange S501a of the cylinder member S501 may have an I-cut shape. Two notches S505 are cut in the outer peripheral portion of the cylinder flange S501a (only one notch is shown in the diagram). The conduit-tube portion S501b at the front end of the cylinder member S501 may be a portion for Luer-lock connection having two cylindrical portions on the inner side and the outer side disposed concentrically. As shown in FIG. 4B(b), the protruding portion S501c having a ring shape and a plurality of ribs 501d extended toward an outer side from the protruding portion S501c may be formed on a back surface of the cylinder flange S501a. In FIG. 4B, a syringe in which both the notch S505 and the ribs 501d have been formed in the cylinder flange S501a is illustrated. However, the syringe may have only any one of the notch S505 and the ribs 501b formed therein.

The cylinder member may be made of a resin material or a material such as glass. A front-end portion of the cylinder member may have a tapered-shape with a diameter narrowing progressively. The conduit-tube portion S501b may be connected directly or may be connected via a connecting member such as a connector.

It is preferable that at least a portion accommodating the chemical liquid (liquid) of the cylinder member is light-transmitting, or in other words, transparent or opaque so that it is possible to confirm visually an amount of the chemical liquid inside. A scale that can display the remaining amount of the chemical liquid may have been provided to the outer peripheral surface of the cylinder member.

The maximum capacity of the cylinder member (in other words, the maximum capacity of the syringe) is not limited in particular, and is determined according to the type and application of a chemical liquid that is accommodated. As an example, for injecting a contrast medium, the maximum capacity is about 50 ml to 200 ml in a large number of cases. However, the maximum capacity is not limited to this and may be about 10 ml to 500 ml.

A material for a gasket portion of the piston member is not limited in particular provided that it is an elastic material which slides liquid-tightly in an axial direction inside the cylinder member. As an elastic material, various rubber materials such as natural rubber, isoprene rubber, butadiene rubber, styrene-butadiene rubber, butyl rubber, silicone rubber, fluorine rubber, and acrylic rubber, and various thermoplastic elastomers of polyurethane, polyester, polyamide and the like, may be used. One or a plurality of sealing members having a ring shape may be provided to the outer peripheral portion of the gasket portion.

In a case of using two or more syringes, one may be for a contrast medium and the remaining may be for a saline or a contrast medium (having different concentration for example).

[A2. Injection Head]

Figure 2:
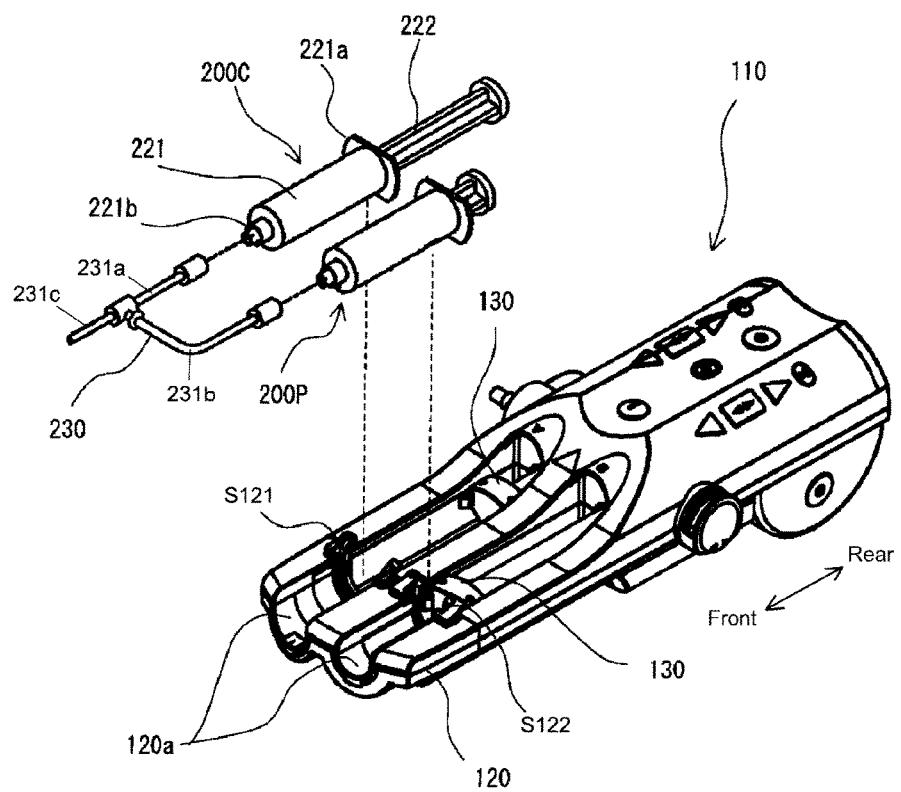
FIG. 2 is a perspective view showing an injection head and a chemical liquid syringe that is to be mounted thereon.

The injection head 110, as shown in FIG. 2, may include a housing extended to be long in a frontward-rearward direction for example. Two recesses 120a for mounting the syringes 200C and 200P respectively are formed in an upper-surface front-end side of the housing. The recess 120a is a portion functioning as a syringe holding portion.

The syringe 200 may be mounted directly in the recess 120a or may be mounted via a predetermined syringe adapter. In FIG. 2, a cylinder flanges 221a of each syringe 200 and syringe adapters S121 and S122 holding an adjacent portion thereof are illustrated as an example. The shape and function of the syringe adapter is not limited specifically, and may be arbitrary.

The injection head 110, moreover, as shown in FIG. 2 and FIG. 3, includes a piston-drive mechanism 130 having at least a function of pushing the piston member 222 of the syringe 200. Two piston-drive mechanisms 130 are provided, and each piston-drive mechanism 130 operates independently. The piston-drive mechanism 130 may have a function of moving the piston member 222 backward for suctioning the chemical liquid into the syringe. The two piston-drive mechanisms 130 may be operated simultaneously or at different timings.

The piston-drive mechanism 130 is not illustrated in detail in the diagram, but may include a drive motor (not shown), a motion conversion mechanism (not shown) which converts a rotation output of the drive motor to a linear motion, and a syringe presser (ram member) which is connected to the motion conversion mechanism, and makes the piston member 222 move forward and/or backward. A known mechanism which is generally used in a chemical liquid injection apparatus can be used as such piston-drive mechanism.

The piston-drive mechanism 130 may include a load cell (not shown) for detecting a force exerted by the syringe presser for pushing the piston member 220. By using detection result of the load cell, it is possible to calculate an estimate value of a pressure of the chemical liquid at the time of injecting. The estimate value is calculated upon taking into consideration a size of the needle, a concentration of the chemical liquid, and injecting conditions. As another method, without using the load cell (not shown), the pressure may be calculated based on a motor current of the drive motor (not shown). A pressure sensor other than the load cell may be used.

In a case in which, the IC tag 225 is put on the syringe, the injection head 110, as shown in FIG. 3, may include a reader/writer 145 which reads the information of the IC tag 225 and/or writes information in the IC tag 225. The reader/writer 145 may be provided to the recess 120a in which, the syringe 200 is mounted. The reader/writer 145 may have only a function of reading the information of the IC tag 225.

The injection head 110, as shown in FIG. 3, may include a control section 144 for controlling an operation of the piston-drive mechanism 130 and the reader/writer 145. Moreover, the injection head 110 may include a storage section 146 which temporarily stores the information read from the IC tag 225.

An upper surface and a side surface of the housing of the injection head 110 are provided with a plurality of physical buttons for carrying out various operations in the injection head 110. Some of the physical buttons may be let to emit light for notifying predetermined information to an operator.

[A3. Stand]

The movable stand 111 may include a caster portion provide with a plurality of wheels, and a supporting column fitted to an upper portion of the caster portion, and the injection head 110 may be held at an upper portion of the supporting column. The supporting column may be curved in the form of English alphabet S or may be straight. Moreover, the supporting column may be stretchable (expandable and contractible) or may not be stretchable (expandable and contractible). The stand 111 may revolvably hold the injection head 110 around a horizontal axis and/or a vertical axis.

Or, the injection head 110 may be held by a so-called arm suspended from the ceiling. The arm suspended from the ceiling (holding apparatus suspended from ceiling) may include a fixed portion that is to be fixed to the ceiling, an arm portion with multiple joints extended from the fixed portion, and a head fixing portion formed at a distal-end portion of the arm portion.

The movable stand 111 and the arm suspended from the ceiling may be nonmagnetic. The movable stand 111 and the arm suspended from the ceiling may be arranged to support almost a central portion of a frontward-rearward direction of the injection head 110, or to pivotably support the injection head 110.

[A4. Console]

The console 150 may be used in an operation room adjacent to an examination room. The console 150 includes a display unit 151 which displays a predetermined images, an operation panel 159 provided to a front surface of the housing, and a control circuit (described below in detail) disposed inside the housing. The operation panel 159 is a portion on which, one or a plurality of physical buttons are disposed, and is to be operated by a user. The display unit 151 may by a touch-panel display or only a display. The console 150 may include a speaker (not shown) etc. for outputting sound and/or voice.

The console 150, in a block diagram in FIG. 3, includes a control section 153 which controls an operation of each portion, a storage section 154 in which various data is stored, and an interface terminal 158 for connecting predetermined external equipment. The console 150 may include an interface for connecting to injection head 110 and an interface for connecting to an imaging apparatus. The console 150 may include a hand unit 157 (not shown in FIG. 1) that is operated by hands of the user. Each component is electrically connected to the control section 153. The control section 153 can be composed as a hardware (a microcomputer for example) having a processor and a memory and the like. An arrangement can be made such that the processor is caused to read a predetermined computer program, and an operation is carried out according to the predetermined computer program.

Data such as data of an image displayed on the display unit 151 may be stored in the storage section 154. Moreover, an algorithm including calculating formulae for setting injecting conditions and data of injection protocol may be stored in the storage section 154. The injection protocol is a protocol indicating what type of chemical liquid, in how much quantity and at what speed is to be injected. The injection rate may be constant or may change according to time. In a case of injecting a contrast medium and a saline, the injection protocol includes information of order in which the chemical liquids are to be injected.

Such information about the injection protocol may have been stored in advance in the storage section 154, or may be input from the external equipment connected via the interface terminal 158. Moreover, the console 159 may have a slot (not shown), and information may be input from an external storage medium inserted into the slot. The storage section 154 is a computer readable medium, and is realized by an HDD (Hard Disk Drive), and SSD (Solid State Drive), or a memory. The memory may be a detachable medium.

The following modifications may be made in a composition of the chemical liquid injection apparatus:

(b1) The injection head 110 and the console 150, without being connected by the cable 102, may be connected via a communication unit of a wireless type. In this case, the communication unit may be attached externally to the injection head 110 or may be built-in. Similarly, the communication unit may be attached externally to the console 150, or may be built-in.

(b2) The chemical liquid injection apparatus 100 and an imaging apparatus 300 may be connected by a wired connection or a wireless connection. Specifically, the console 150 may be connected to the imaging apparatus 300 by a wired connection or a wireless connection. Moreover, the injection head 110 may be connected to the imaging apparatus 300 by a wired connection or a wireless connection.

(b3) The injection head having two syringes mounted thereon has been described above. However, the injection head may have only one syringe mounted thereon.

(b4) The chemical liquid injection apparatus 100, without being limited for CT examination, may be let to be an apparatus for MR examination, angiographic examination, and sonographic diagnosis.

(b5) As a pattern of injecting a contrast medium, a variable pattern in which, the injection rate is reduced linearly and thereafter maintained to be constant and/or a variable pattern in which, the injection rate is reduced linearly and thereafter again increased linearly, can be used.

(b6) The chemical liquid injection apparatus in which, the injection head and the console are separate as shown in FIG. 1 has been described above. However, the chemical liquid injection apparatus may be an injecting apparatus as described below:

A chemical liquid injection apparatus in which, the injection head and the console are integrated, or in other words, a chemical liquid injection apparatus in which, setting of the injection protocol, display of various states while injecting a chemical liquid, and an operation control of the piston-drive mechanism are carried out by one apparatus;

A chemical liquid injection apparatus in which, the injection head and the console are integrated, further including a separate battery unit. Such battery unit may be an AC power source. The power source may be kept at an arbitrary location in the examination room (for example), or may be held by a portion of the movable stand;

A chemical liquid injection apparatus in which, a predetermined operation of the chemical liquid injection apparatus can be controlled from outside of the examination room by using a wired or wireless remote controller. In this case, the wireless control may be carried out by using infrared rays, wireless LAN (local area network), Wi-Fi (registered trademark), Bluetooth (registered trademark), and ZigBee (registered trademark);

An operation to be controlled may be any operation including putting ON/OFF power supply of the apparatus for example. As another example, start or stop of an arbitrary operation of the injection head may be controlled by a remote controller;

A chemical liquid injection apparatus in which, the injection head and the console are separate, but the injection head is provided with a sub-display;

The sub-display may be attached to the injection head or may be separate from the injection head but disposed near the injection head. As an example, the injection head and the sub-display may be disposed to be mutually adjacent at the upper portion of the movable stand; or A chemical liquid injection apparatus in which, a control unit with a small-sized console is disposed near the injection head. Such control unit is held on the movable stand together with the injection head. Or, such control unit is held by an arm that is suspended from the ceiling together with the injection head.

(Imaging Apparatus)

The imaging apparatus 300 may be an apparatus such as CT scanner, MRI apparatus, PET apparatus, or angiography apparatus. The imaging apparatus 300, as shown in FIG. 3, may include an imaging section 303b which captures a perspective image of a patient, a bed 304 for the patient, and a control section 303a which controls operations thereof.

[A5. Leak Detection System]

Figure 5:
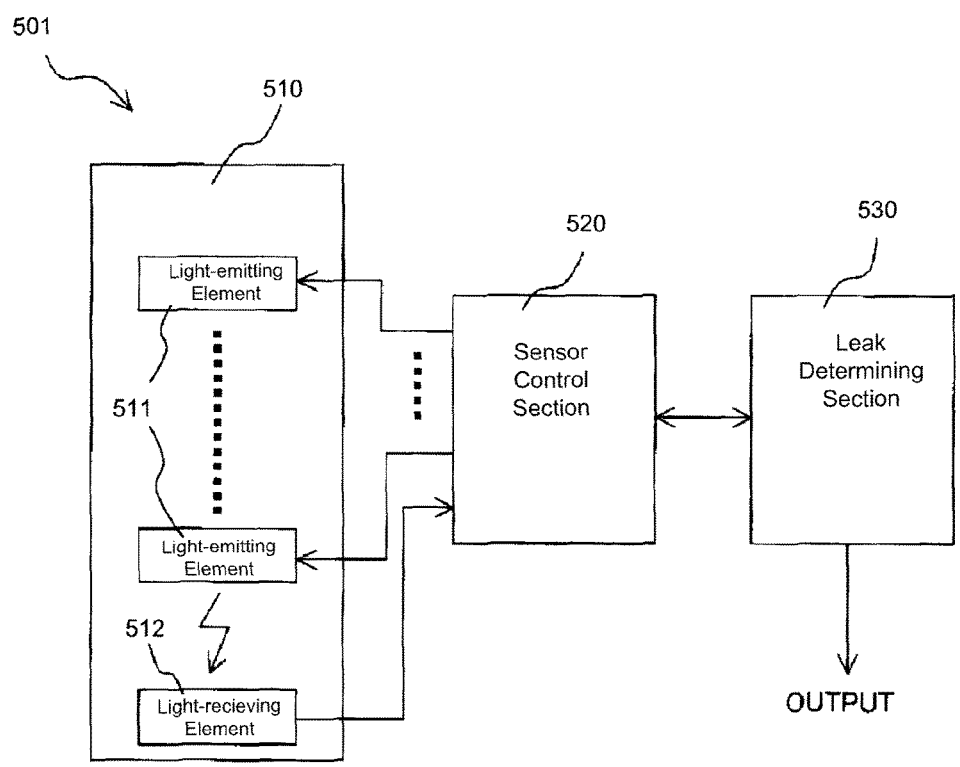
FIG. 5 is a block diagram showing a configuration of a leak detecting sensor.

A leak detection system 501 which includes a sensor head 510, a sensor control section 520, and a leak determining section 530 is shown in FIG. 5.

(Sensor Head)

The sensor head 510 is to be used in close contact or in proximity of a portion of the patient's body at the time of injecting chemical liquid. The sensor head 510 includes a housing 515 (refer to FIG. 6), and light-emitting elements 511 and a light-receiving element 512 at an interior of the housing 515. An emission wavelength of the light-emitting element 511 is in a range of 780 nm to 950 nm for example, and more preferably in a range of 850 nm to 900 nm.

The light-emitting element 511 may be an element which irradiates light of a predetermined wavelength, and specifically, a light-emitting diode which irradiates infrared rays. The light-receiving element 512 is an element which converts optical energy to electric energy. The element may be an element which can achieve an electrical output by receiving at least light of a wavelength irradiated by the light-emitting element 511. The light-receiving element 512, specifically, may be a phototransistor.

The sensor control section 520 controls an operation of the light-emitting elements 511 and the light-receiving element 512. The control section 520 controls as to which light-emitting diode 511 is to be driven at which timing in accordance with a predetermined procedure. The leak determining section 530 determines leakage of a chemical liquid based on a change in an electrical output value from the light-receiving element 512. The leak determining section 530, when has determined that there is a leakage, outputs a leak determining signal which is an electric signal. The control section and the leak determining sections can be configured as a hardware (for example, a microcomputer for example) having a processor and a memory.

Figure 6:
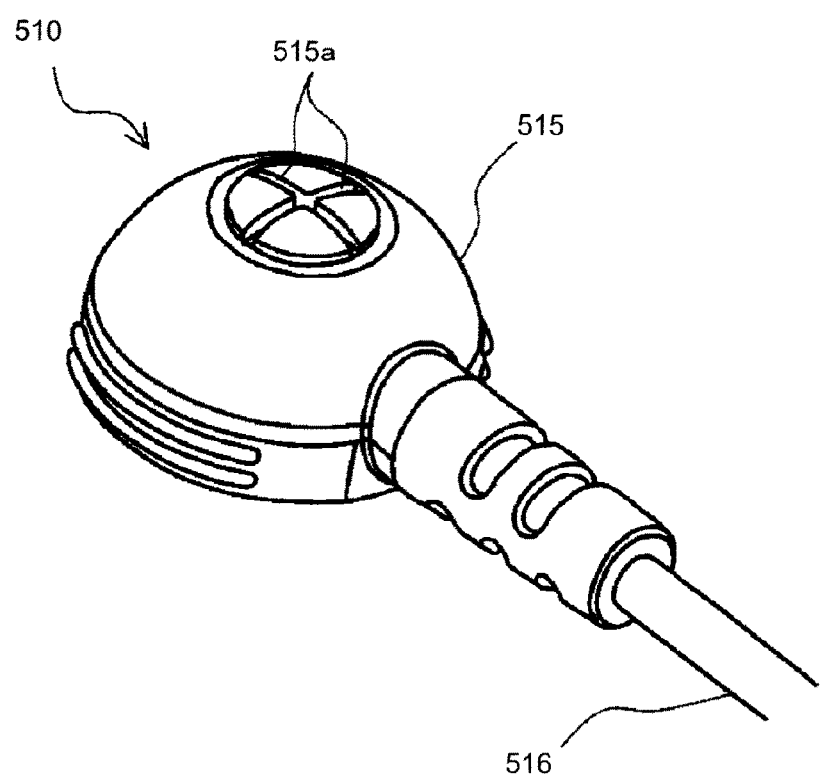
FIG. 6 is a perspective view when a sensor head according to a first example is viewed from an upper side.
Figure 7:
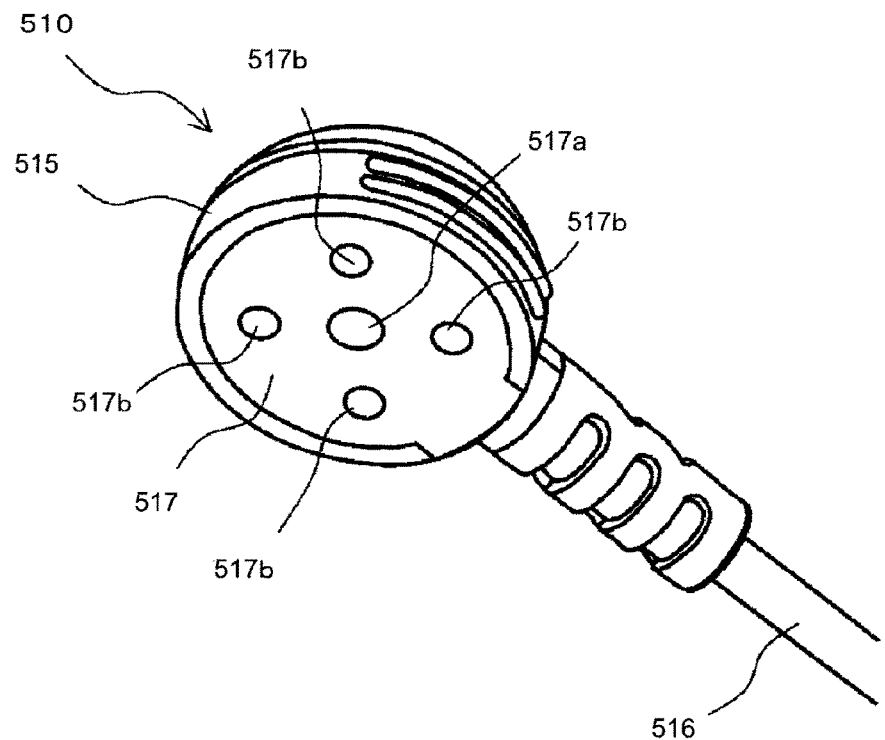
FIG. 7 is a perspective view when the sensor head shown in FIG. 6 is viewed from a sensor-surface side thereof.
Figure 8:
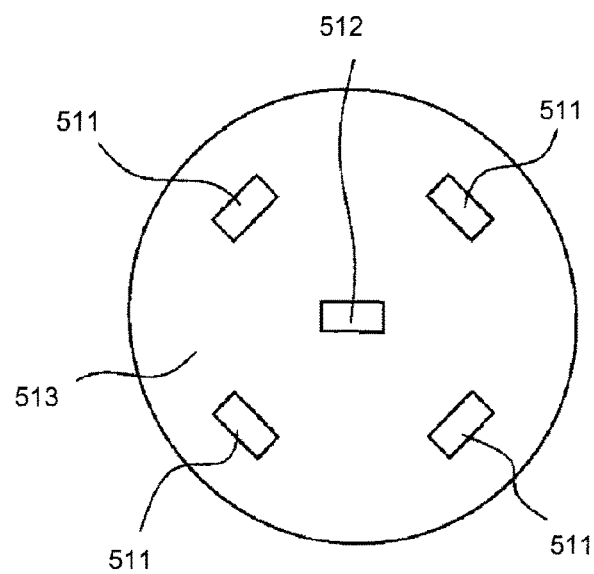
FIG. 8 is a diagram showing an example of arrangement of light-emitting elements and a light-receiving element.
Figure 9:
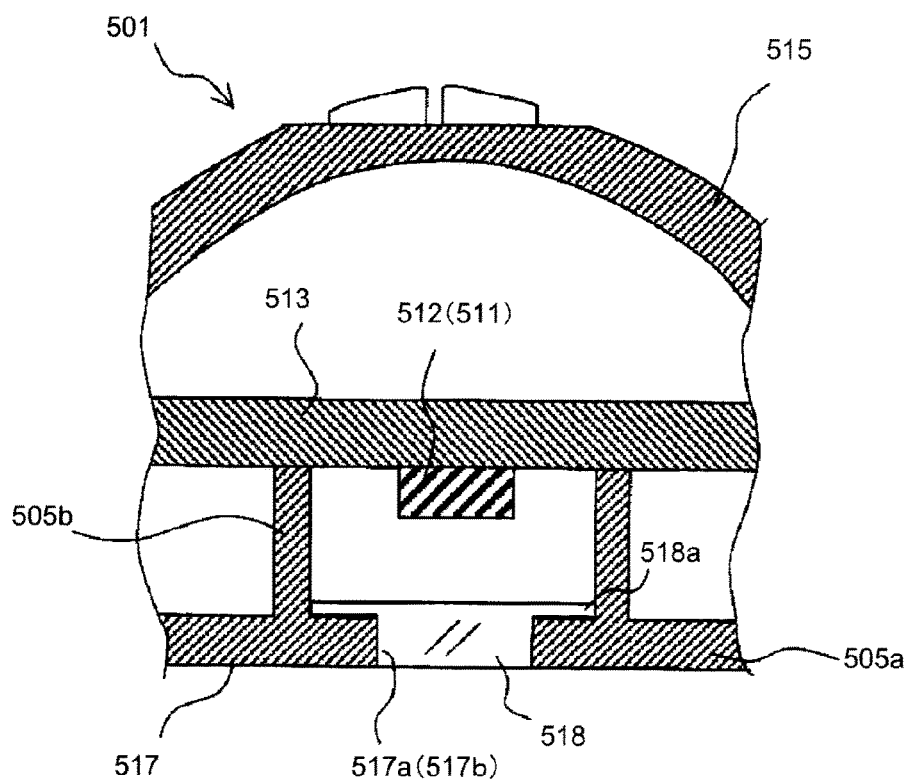
FIG. 9 is a simplified longitudinal sectional view of the sensor head shown in FIG. 6, at a position through the light-receiving element.

The sensor head 510, as shown in FIG. 6 to FIG. 8, includes a sensor surface 517 which is let to be in close contact with the patient at the time of using. The sensor surface 517 may be a flat surface. A shape of the sensor surface 517 may be a circular shape or substantially circular shape. The sensor head 510 may include the housing 515 made of a resin for example, and an upper surface of the housing may be dome-shaped for example. The housing 515 may be formed as a closed case, and the plurality of light-emitting elements 511 and one light-receiving element 512 may have been disposed at the interior thereof. As shown in FIG. 8, four light-emitting elements 511 and one light-receiving element 512 may have been disposed. The light-emitting elements 511 and the light-receiving element 512, as shown in FIG. 9, may have been mounted on a substrate 513, and fixed inside the housing 515. The light-receiving element 512 may have been mounted at a position corresponding to a center of the sensor surface 517 of the housing 515. The four light-emitting elements 511 may have been mounted at surrounding positions at equal angular intervals and at equal distances from the light-receiving element 512. By such arrangement, a center of a light emitting area of the light-emitting elements 511 and a center of a light receiving area of the light-receiving element 512 coincide. The four light-emitting elements 511 may have been disposed at 90 degree intervals (circumferential direction) with the light-receiving element 512 as a center. The substrate 513 may have been fixed such that the light-receiving element 512 is positioned on an intersection point of two grooves 515a (refer to FIG. 2). Particularly, the substrate 513 may be disposed such that the four light-emitting elements 511 are line-symmetric with respect to the two grooves 15a respectively.

The housing 515, in the sensor surface 517, may have an opening portion 517a at a center and four opening portions 517b in a surrounding thereof. The opening portion 517a at the center is formed at a position facing the light-receiving element 512 disposed inside the housing, and accordingly, the light-receiving element 512 receives light incident inside the housing upon passing through the opening portion 517a. In view of such type of light reception, it is preferable that the housing 515 is made of a material that does not allow light from the outside to be transmitted through. The housing 515 may be formed of a material that transmits light and an inner surface of the housing may shield light by paint, or the housing 515 may be a combination of the two. Each opening portion 517b may have been disposed to be facing the corresponding light-emitting element 511. Light from each light-emitting element 511 is irradiated to the outside of the housing through the opening portion 517b. A range of irradiation of light by the light-emitting element 511 and a range of reception of light by the light-receiving element 512 have an effect on a shape of the opening portions 517b and 517a respectively. From a view point of an efficient use of light irradiated from the light-emitting element 511, it is preferable that the opening portions 517a and 517b have a circular shape.

As shown in FIG. 9, a light transmitting member 518 may have been fitted in the opening 517a. The light transmitting member 518 transmits light irradiated by the light-emitting element 511. The light transmitting member 518 may have a cross-section of a size and a shape same as a size and a shape of the opening portion 517a. In this case, there is no gap between an inner peripheral surface of the opening portion 517a and an outer peripheral surface of the light transmitting member 518. The light transmitting member 518 may have a flange portion 518a at one end in a direction of thickness thereof. The light transmitting member 518 is held by an inner surface of the housing 515 such that the light transmitting member 518 does not come off the opening portion 517a by fitting upon positioning the flange portion 518a at an inner side of the housing 515, and adhering the flange portion 518a to the inner surface of the housing 515. An adhesive agent or an adhesive tape can be used for attaching the flange portion 518a. Moreover, by the light transmitting member 518 having the flange portion 518a, a structure is such that an extraneous matter or a chemical liquid is hard to enter the interior of the housing 515. A thickness of a portion of the light transmitting member 518 excluding the flange portion 518a may be let to be same as a thickness of a bottom wall 505a of the housing 515, and accordingly, it is preferable that the bottom surface of the housing 515 and a bottom surface of the light transmitting member 518 are positioned on the same plane.

The structure related to the opening portion 517a was described in FIG. 9, and the opening portion 517b may have a similar arrangement. In other words, the light transmitting member 518 may have been fitted in the opening portion 517b from the inner side of the housing 515. By the light transmitting member 518 being fitted in the opening portions 517a and 517b, the overall bottom surface of the housing 515 may be formed as the flat sensor surface 517 including the bottom surface of the light transmitting member 518.

Figure 10:
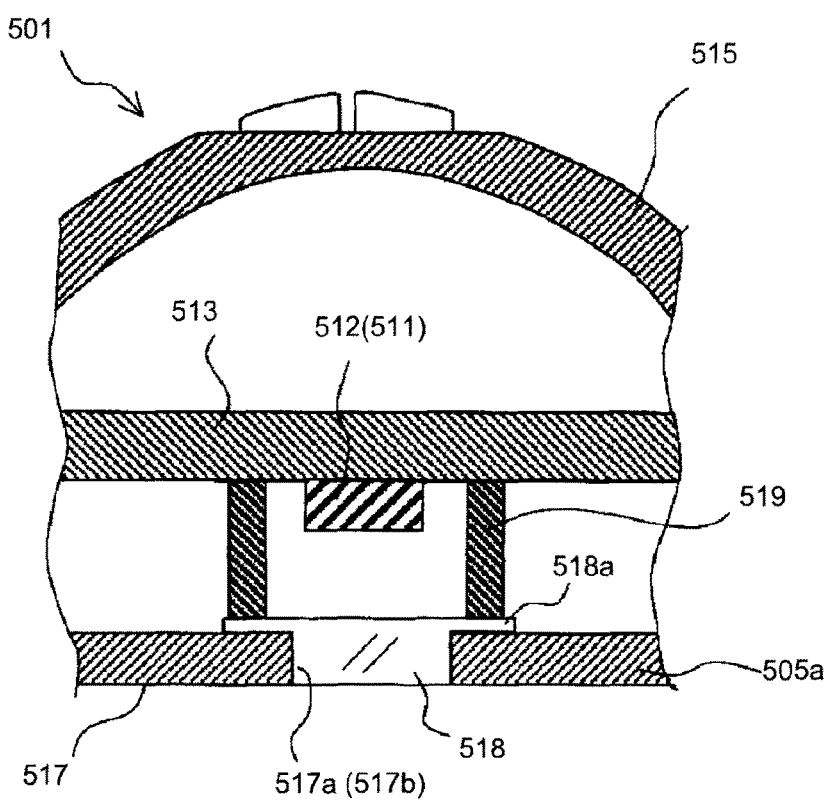
FIG. 10 is a longitudinal sectional view showing a modified example of a structure holding a light transmitting member in the sensor head shown in FIG. 6.

In the description above, although the light transmitting member 518 has been fixed to the inner surface of the housing 515 by adhering, the structure may be let to be as shown in FIG. 10. In other words, in this example, a holding member 519 is formed in the housing 515. The holding member 519 is positioned between the bottom wall 505a of the housing 515, and pushes the flange portion 518a toward the bottom wall 505a. Accordingly, the light transmitting member 518 is held by the inner surface of the housing 515. By using the flange portion 518a of the light transmitting member 518, the light transmitting member 518 can be fixed to the housing 515 by various methods.

Regarding an internal structure of the housing 515, as shown in FIG. 9, a partition wall 505b which surrounds an entire periphery of the opening portion 517a (each opening portion 517b) and the light-receiving element 512 (each light-emitting element 511) facing the opening portion 517a may be formed. The partition wall 505b may be extended from the bottom wall 505a of the housing 515 toward the substrate 513. By such partition wall 505b, it is possible to separate each of a path of light irradiated from each light-emitting element 511 to outside of the housing 515 upon passing through the opening portion 517 and a path of light reaching the light-receiving element 512 upon passing through the opening portion 517a as independent paths. As a result, it is possible to improve an accuracy of detection of leakage. Even in a structure for holding the light transmitting member 518 shown in FIG. 10, similarly, the holding member 519 can be formed to surround the entire periphery of the opening portion 517a (opening portion 517b) and the light-receiving element 512 (light-emitting element 511).

Referring again to FIG. 6 and FIG. 7, a cable 516 that transmits an electric signal is extended from the housing 515. The sensor control section 520 shown in FIG. 4 (or a control circuit unit in which, the sensor control section 520 and the leak determining section 530 are integrated) may be electrically connected to the sensor head 510 via the cable 516.

The sensor control section 520 and the leak determining section 530 may have been formed separately from the sensor head 510 as an independent unit in which the two are combined, or may be incorporated into the sensor head 510. Or, the sensor control section 520 and the leak determining section 530 may be formed as one of the functions of the chemical liquid injection apparatus that injects a chemical liquid into the patient, to be used together with the leak detection system 501. In a case in which, the sensor control section 520 and the leak determining section 530 are to be incorporated into the sensor head 510, the cable 516 may be used as a cable for power supply. Furthermore, the sensor control section 520 and the leak determining section 530 may have been formed as separate units, and one of the two may be incorporated into the sensor head 510 and formed as one of the functions of the chemical liquid injection apparatus. One of the sensor control section 520 and the leak determining section 530 can also be formed separately from the sensor head 510 and the chemical liquid injection apparatus. In the present invention, the leak detecting sensor 501 and the chemical liquid injection apparatus combined together will be called as a chemical liquid injection system.

Regarding the leak detecting sensor, the following modifications may be made.

(c1) In a case in which, the sensor control section 520 and the leak determining section 530 are independent units, for informing the result of determination by the leak determining section 530 to the operator, the leak detecting sensor 501 may further include a display unit and/or a voice output unit.

(c2) Whereas, in a case in which, the sensor control section 520 and the leak determining section 530 are formed as one of the functions of the chemical liquid injection apparatus, since the sensor control section 520 and the leak determining section 530 are incorporated into the chemical liquid injection apparatus, the sensor head 510 is to be connected to the chemical liquid injection apparatus via the cable 516. The cable 516 may be detachably connected to the chemical liquid injection apparatus by an appropriate connector (not shown).

(c3) A power-supply unit (not shown) is connected to the leak detecting sensor 501, and the leak detecting sensor 501 is operated by an electric power supplied from the power-supply unit. As the power supply unit, a direct-current (DC) power supply to which an alternating current (AC) is input by a commercial power supply and which outputs a predetermined direct current (DC), and batteries such as a dry cell, a secondary cell, and a fuel cell can be used.

(c4) Generally, a dedicated power supply is arranged for operating the leak detecting sensor 501. However, in a case in which, the sensor control section 520 has been incorporated into the chemical liquid injection apparatus, by using a power supply unit that supplies the electric power to the chemical liquid injection apparatus in common with the chemical liquid injection apparatus, the electric power can be supplied to the sensor control section 520 from the power supply unit for the chemical liquid injection apparatus.

(c5) It is preferable to connect the leak determining section 530 to a control section of the chemical liquid injection apparatus, and to input a leak detection signal that has been output from the leak determining section 530 to the control section of the chemical liquid injection apparatus. By doing so, the control section of the chemical liquid injection apparatus stops an operation of injecting a chemical liquid based on the leak detection signal, thereby making it possible to suppress the leakage to the minimum.

(c6) Such leak detecting sensor may have all the functions built-in in the sensor head 510, or some of the functions included in a unit separate from the sensor head 510 and some of the functions incorporated in the chemical liquid injection apparatus. Or, some of the functions may be included in a unit separate from the sensor head 510 and some of the remaining functions may be incorporated in the chemical liquid injection apparatus. The sensor unit 510 and the unit separate from the sensor unit 510 (including the unit incorporated into the chemical liquid injection apparatus) may be connected by a wired connection via the aforementioned cable 516, or may be connected by a wireless connection.

(c7) Although a case in which the number of light-emitting elements 511 is four has been described in the embodiment, the number of light-emitting elements 11 can be let to be two, three, or five and more provided that the light-emitting elements 511 are disposed to be surrounding the light-receiving element 512. Even in a case in which, the number of light-emitting elements 511 is four or more than four, each light-emitting element 511 can be driven to emit light at a different timing, or the light-emitting elements 11 can be divided into a plurality of groups, each group including a plurality of light-emitting elements 11, and each group can be driven to emit light at a different timing.

(Sensor Head According to Another Embodiment)

Figure 11:
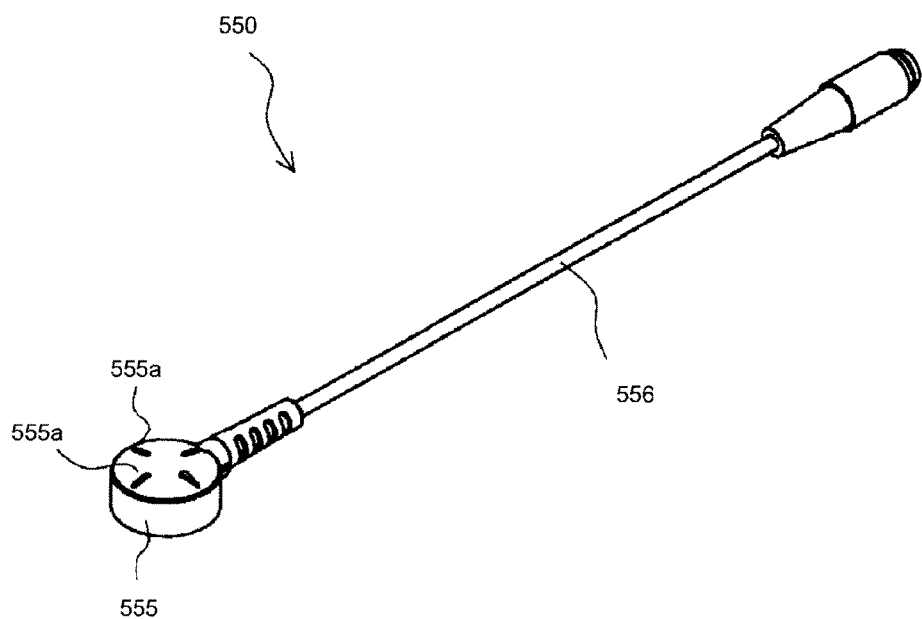
FIG. 11 is a perspective view when a sensor head according to a second example is viewed from an upper side.
Figure 12:
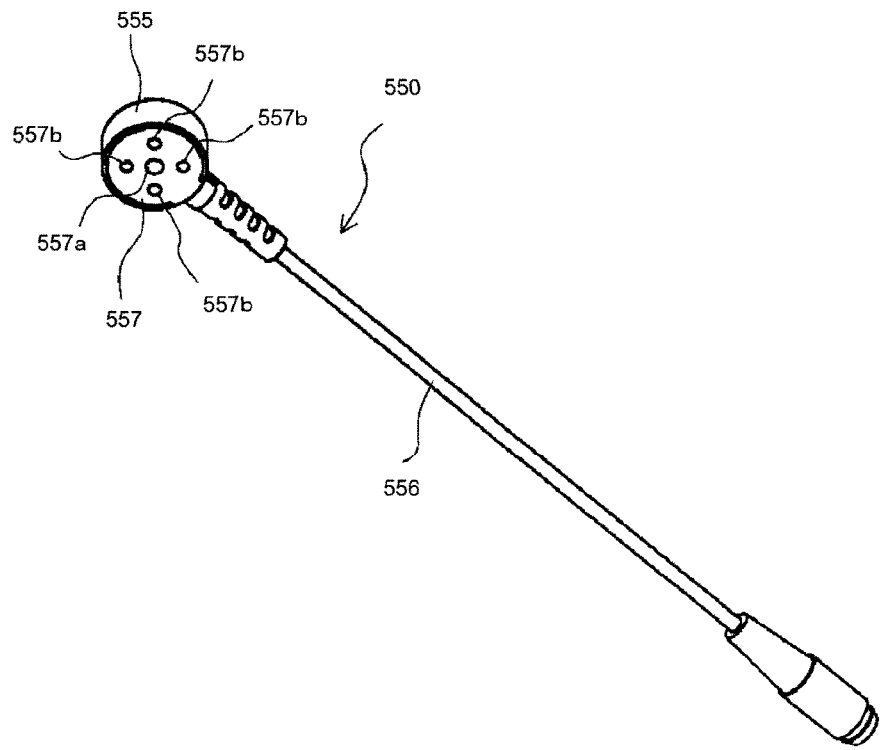
FIG. 12 is a perspective view when the sensor head shown in FIG. 11 is viewed from a sensor-surface side.
Figure 13:
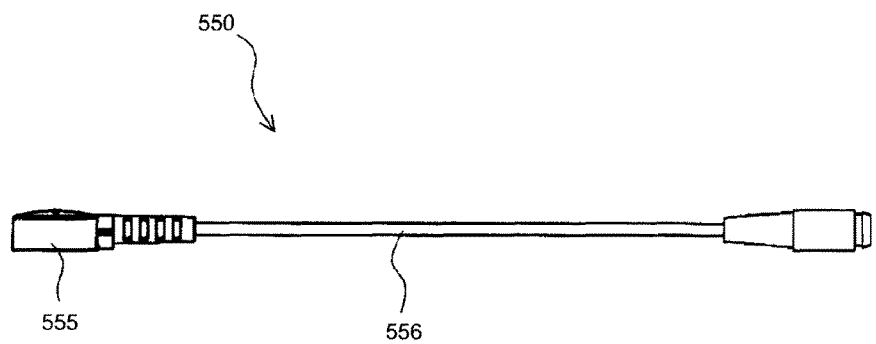
FIG. 13 is a side view of the sensor head shown in FIG. 11.

Moreover, a sensor head 550 having a shape of a housing as shown in FIG. 11 to FIG. 13 may be used. The sensor head 550 includes a housing 555 having a shape of a flat circular column with one end surface as a sensor surface 557. A plurality of light-emitting elements (not shown) and one light-receiving element (not shown) are disposed inside the housing 555 similarly as in the abovementioned embodiment. An opening portion 557a corresponding to the light-receiving element and a plurality of opening portions 557b corresponding to the light-emitting elements are formed on the sensor surface 557 to be brought into contact with the patient. A plurality of protrusions 555a to be used for positioning the sensor head 550 and the injection needle while fixing the sensor head 550 to the patient is formed in a cross shape. The light-emitting elements and the light-receiving element disposed inside the housing 555 can be connected to the chemical liquid injection apparatus via a cable 556. Regarding an internal structure of the sensor head 550, the internal structure of the abovementioned sensor head 510 can be used partially or fully, and repetitive description thereof is omitted here.

[B1. Sensor Pad Kit]

Figure 14:
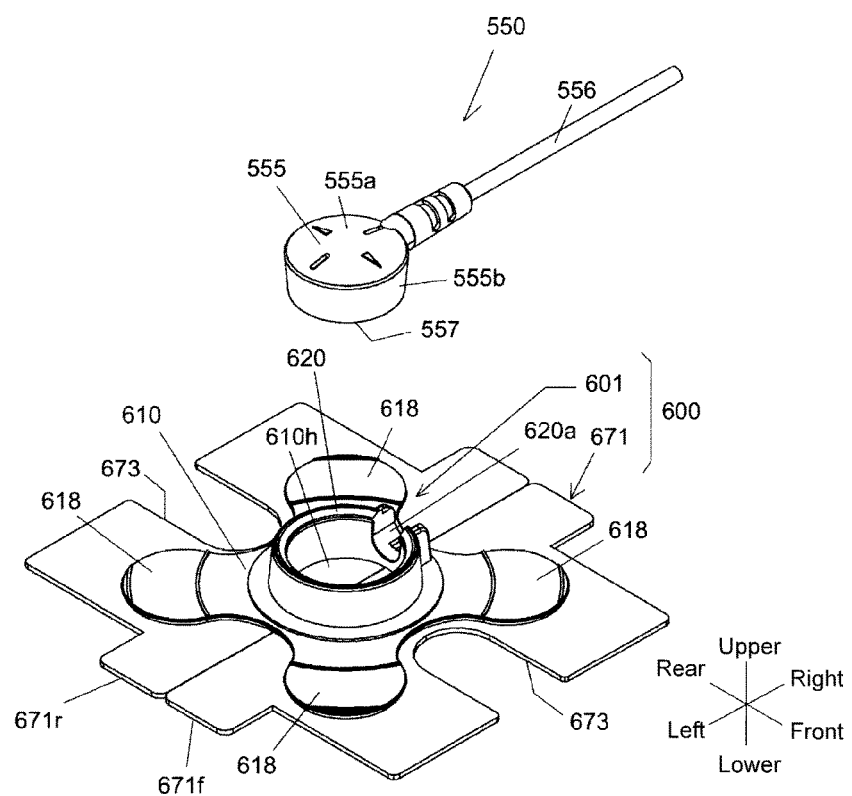
FIG. 14 is a perspective view showing a sensor pad kit and a sensor head to be mounted thereon.

A sensor pad kit 600, as shown in FIG. 14, includes a sensor pad 601 which is flexible and is to be attached to the body of a patient, and a peelable film 671 which is stuck to a back surface of the sensor pad 601. Although it is omitted in the diagram, the sensor pad kit 600 may further include a packaging bag which accommodates the sensor pad 601 in a state of the peelable film 671 stuck thereto. The sensor pad kit 600 contained in the packaging bag in such manner may be treated as a disposable product.

The packaging bag may be of a transparent material for example. Moreover, information such as product number and date may have been printed on a portion of the packaging bag. The sensor pad kit 600 may be sealed in the packaging bag in a factory and supplied to hospital facilities.

The sensor pad 601 holds the housing 555 of the sensor head 550, and fixes the sensor head 550 to the body of a patient. The sensor pad 601 includes a flexible base member 610 in the form of a seal and a sensor holding portion 620 formed on a portion of the flexible base member 610. The sensor holding portion 620 may have been formed at a substantially central portion of the flexible base member 610 for example.

The flexible base member 610 and the sensor holding portion 620 may have been formed by different members or may have been formed integrally. In a case in which, the flexible base member 610 and the sensor holding portion 620 have been formed as different members, a material for the two may be the same or may be different. In this example, the flexible base member 610 and the sensor holding portion 620 are formed integrally. The material of the sensor pad 601 may be an elastic material for example (such as rubber, elastomer and the like). The sensor pad 601 may be a component formed by a metal mold.

Figure 15:
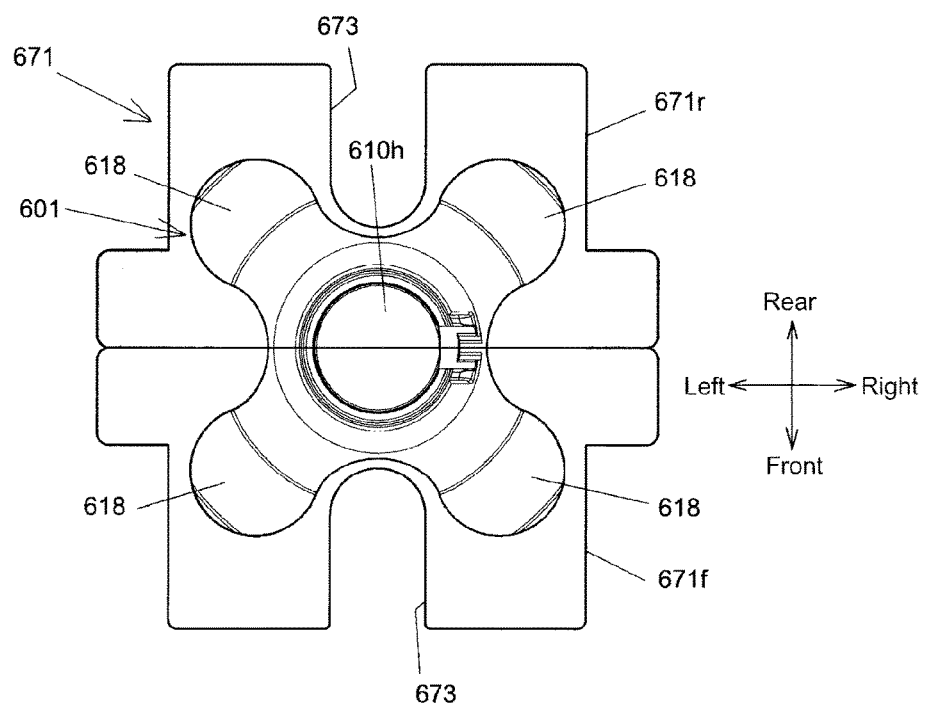
FIG. 15 is a plan view of a sensor pad stuck on a peelable film.

The flexible base member 610, when viewed from an upper side (in other words, in a plan view) as shown in FIG. 14 and FIG. 15, may include four extended portions 618 extended from a central portion toward an outer side. The four extended portions 618 may have been disposed at intervals of 90° for example. A tip portion of each extended portion 618 may have been formed to have a circular-arc shape, and moreover, a width of the extended portion 618 may have a shape such that a base end side is thinner as compared to a widest portion of a tip side. The number of the extended portions 618 may be let to be two, three, or five or more. One or the plurality of extended portions 618 and another one or the plurality of extended portions may have been formed to have different shapes. Moreover, a flexible base member having a circular shape, an elliptical shape, a rectangular shape, or a polygonal shape, which has no extended portion 618 may be used. It is to be noted that such arrangement may be applied to another embodiment illustrated in another diagram.

One opening portion 610h is formed at a substantially central portion of the sensor pad 601. The opening portion 610h is for letting the sensor surface 557 to face the body surface of the patient when the sensor head 550 has been mounted as will be described later.

The sensor surface 557 may by arranged to make a close contact with the body surface of the patient or may be arranged to be in proximity of the body surface of the patient. The opening portion 610h may have a circular shape, an elliptical shape, a rectangular shape, or a polygonal contour shape. The description, in a case in which an opening portion (referred to as an opening portion facing a sensor surface of a sensor device) of a member other than the flexible base member 610 in the present application, may be applied to such opening.

Figure 16:
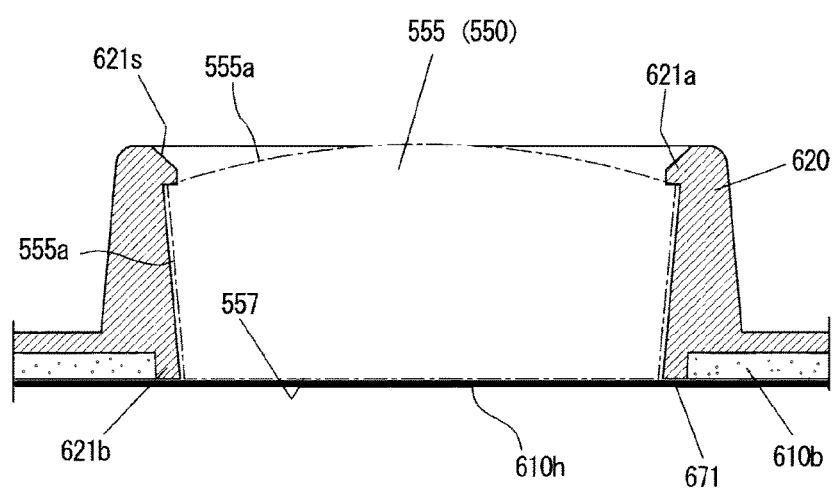
FIG. 16 is a longitudinal sectional view of a sensor holding portion of the sensor pad, and a surrounding portion thereof.

The sensor holding portion 620, as shown in FIG. 14, is formed to be substantially circular cylindrical shaped corresponding to the housing 555 of the sensor head 550. In this example, the sensor head 550 as mentioned above, has an external shape of a short circular column as a whole, and has an upper surface 555a, a side-wall portion 555b, and a lower surface (sensor surface) 557. The upper surface 555a may have a shape of a dome protruded upward gently. The side-wall portion 555b may be formed to be straight in a vertical direction, or may be formed to be tapered-shaped progressively narrowing toward a lower side as illustrated in FIG. 16. The sensor holding portion 620 may have a shape corresponding to the shape of the sensor head, and may be formed to have a rectangular frame shape when the shape of the housing of the sensor head is rectangular, and may be may be formed to have a polygonal frame shape when the shape of the housing of the sensor head is polygonal.

As shown in FIG. 14, a recess 620a for the cable 556 of the sensor head 550 to pass may have been formed in a part of the sensor holding portion 620. The recess 620a may have a shape of an English alphabet U when the sensor holding portion 620 is viewed from a side.

The sensor head 550 can be fitted to the sensor holding portion 620 by inserting the sensor head 550 into the sensor holding portion 620 (details described below). For fitting the sensor head 550 by such method, a tapered surface 621s for making it easy to insert the sensor head 550 may be formed at an inlets portion of the sensor holding portion 620 as shown in FIG. 16.

Moreover, it is preferable that a protrusion 621a is formed at the inlet portion of the sensor holding portion 620. The protrusion 621a is a part extended toward an inner side in a radial direction. By such protrusion 621a being formed, a diameter of the inlet portion of the sensor holding portion 620 is formed to be smaller than an outer diameter (the maximum portion) of the sensor head 550.

When inserting the sensor head 550 into the sensor holding portion 620, as the sensor holding portion 620 is spread out toward an outer side in the radial direction (elastic deformation) and the sensor head 550 is inserted further up to a predetermined fixed position (refer to FIG. 16), the protrusion 621a is engaged with a portion (outer peripheral portion of the upper surface for example) of the sensor head 550. The protrusion 621a may have been formed on the entire sensor holding portion 620 (excluding the recess 620a) surrounding the entire periphery of the housing 555. Moreover, one or a plurality of protrusions 621a may have been formed on a part of the sensor holding portion 620.

It is preferable that when the sensor head 550 has been fitted normally, or in other words, when the protrusion 621a is engaged with the sensor head 550, there is a click feeling. Accordingly, the user is able to confirm by feeling and/or visually that the sensor head 550 has been mounted correctly.

Next, a structure on a back surface side of the sensor pad 601 will be described below.

An adhesive layer 610b is provided to a back surface of the sensor pad 610 as shown in FIG. 16. The adhesive layer 610b may be inelastic, such as a double-stick tape, but in this example, a gel-like sheet member having elasticity is used as an example. The sheet member may be adhesive silicone rubber. The thickness of the adhesive layer 610b may be about 0.5 mm to 3.0 mm. The adhesive layer 610b is not limited in particular, and may be formed on an entire back surface of the flexible base member 610 or may be formed on a part of the back surface of the flexible base member 610.

It is preferable that a light-shielding wall 621b which surrounds an external periphery of the opening portion 610h is formed on the back surface of the flexible base member 610 as shown in FIG. 16. The light-shielding wall 621b is a part protruded to a predetermined height (0.1 mm to 3.0 mm for example) from the flat back surface of the flexible base member 610. Or, the light-shielding wall 621b may protrude to a predetermined height (0.1 mm to 3.0 for example) from a back surface of the adhesive layer 610b.

By such light-shielding wall 621b being formed, even in a case in which, the extended portion 618 attached to the body of the patient has come off during leak detection, light from outside is prevented from entering as long as a lower end of the light-shielding wall 621b makes a close contact with the body of the patient. As a result, it is possible to continue the leak detection favorably. The light-shielding wall 621b may have any shape provided that the light shielding wall 621b has such function. The shape may be a circular shape, an elliptical shape, a rectangular shape, and a polygonal shape. Moreover, the shape may be a shape corresponding to the shape of the opening portion 610h.

(Peelable Film)

The peelable film 671 may be a single film as a whole, or may be divided into at least two. The peelable film 671 may be a sheet member made of resin for example. In the example in FIG. 14 and FIG. 15, the peelable film 671 can be divided into a film 671f at front side and a peelable film 671 at rear-side. The two peelable films 671f and 671r may have been divided thoroughly in advance or may have been connected at a certain portion. In this case, the peelable film 671f at front side and the peelable film 671r at rear side may have been formed to be symmetric about a parting line (line-symmetric or point-symmetric with reference to a central portion of the parting line). In a case in which, the peelable film 671f at front side and the peelable film 671r at rear side are formed to be symmetric, the peelable film 671 can be used in any direction. In other words, the peelable film 671f can be used at the front side or the other peelable film 671r can also be used at the front side.

The peelable film 671, as shown in FIG. 14 and FIG. 15, may have a positioning recess 673 for determining a position of attaching the sensor pad 601. The positioning recess 673 may be formed to be U-shaped. Only one positioning recess 673 may be formed in the peelable film 671 or one positioning recess 673 each may be formed in the peelable film 671f at front side and the peelable film 671r at rear side. In the latter case, the shape and/or positions of the two positioning recesses may have been formed to be symmetric about a parting line (line-symmetric or point symmetric with reference to a central portion of the parting line).

Figure 17:
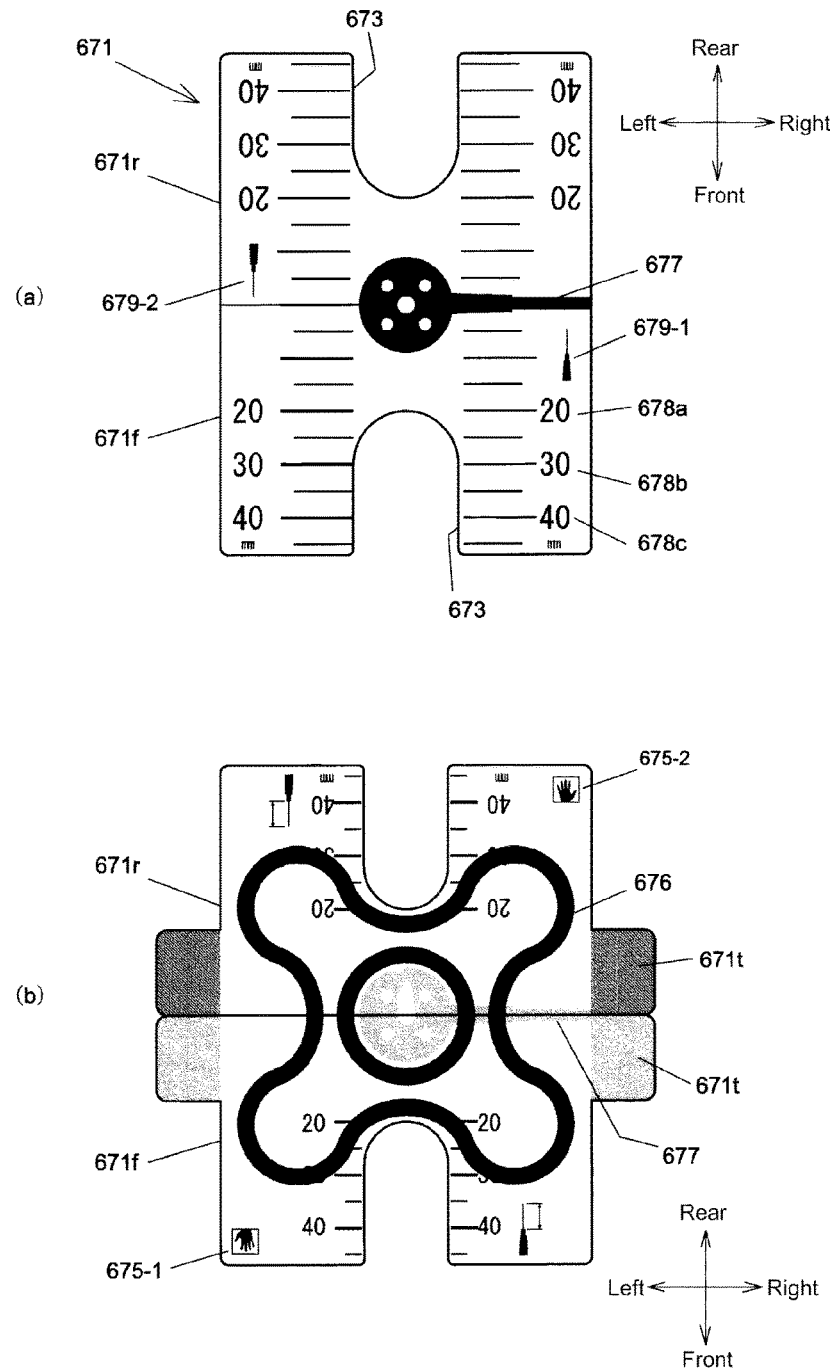
FIG. 17 is a plan view showing an example of the peelable film.

FIG. 17(a) and FIG. 17(b) illustrate a few examples of indicator portions that the peelable film 671 can have. Some of the indicator portions or all of the entire indicator portions below may have been formed to be symmetric about a parting line (line-symmetric or point symmetric with reference to a central portion of the parting line).

As shown in FIG. 17(a), the peelable film 671 may have gauge portions 678a, 678b, and 678c marked as '20' mm, '30' mm, and '40' mm on a side portion of the positioning recess 673. The gauge portions indicate a needle tip of an injection needle punctured into the body of the patient, and a distance of the injection needle from a predetermined reference position (described later in detail).

The peelable film 671, moreover, may have a sensor-head indicator portion 677 which indicates an attaching position of the sensor head 550. The sensor-head indicator portion 677 may be indicated along a parting line of the two peelable films 671f and 671r. The peelable film 671, moreover, may have indicator portions 679-1 and 679-2 indicating direction of the injection needle.

The peelable film 671 in FIG. 17(b) has tabs 671t to be pinched by fingers while removing the peelable films 671f and 671r. One tab 671t each may have been formed on a side portion of the peelable film 671 or the tab 671t may have been formed on only one side portion of the peelable film 671. The tab 671t may have any shape provided that it protrudes from a side-edge portion of the peelable film 671 making it easy to pinch by fingers. As an example, the shape may be a rectangular shape, a polygonal shape, or a semicircular shape.

The peelable film 671 in FIG. 17(b) may have indicator portions 675-1 and 675-2. In a case in which, the peelable film 671 is to be stuck to patient's arm, the indicator portion 675 may be a picture of a palm of the hand as an example. One of the indicator portions 675-1 and 675-2 may have been provided to each of the peelable films 671r and 671f.

Figure 18:
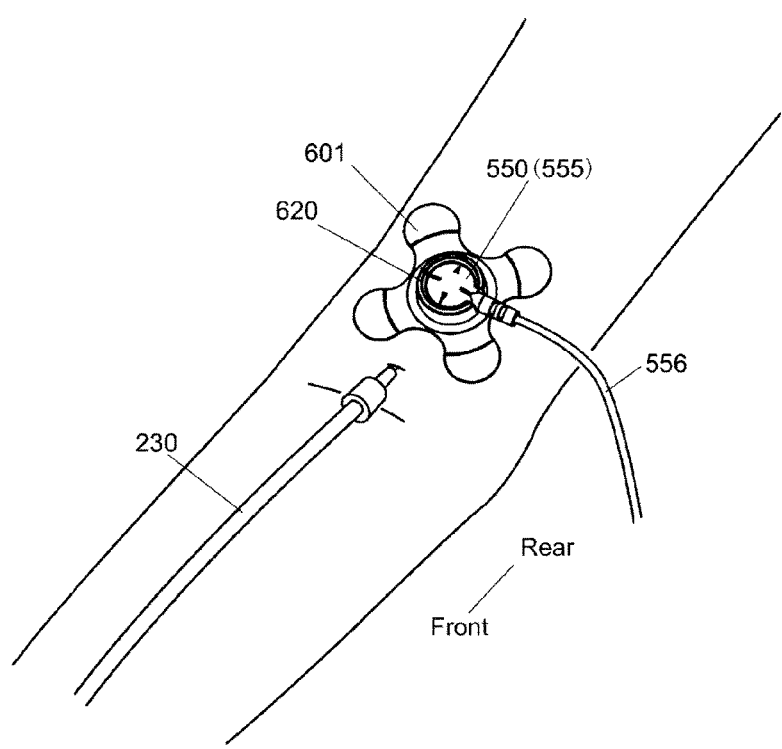
FIG. 18 is a perspective view showing a state in which, the sensor head is attached to an arm of a patient by using the sensor pad.
Figure 19:
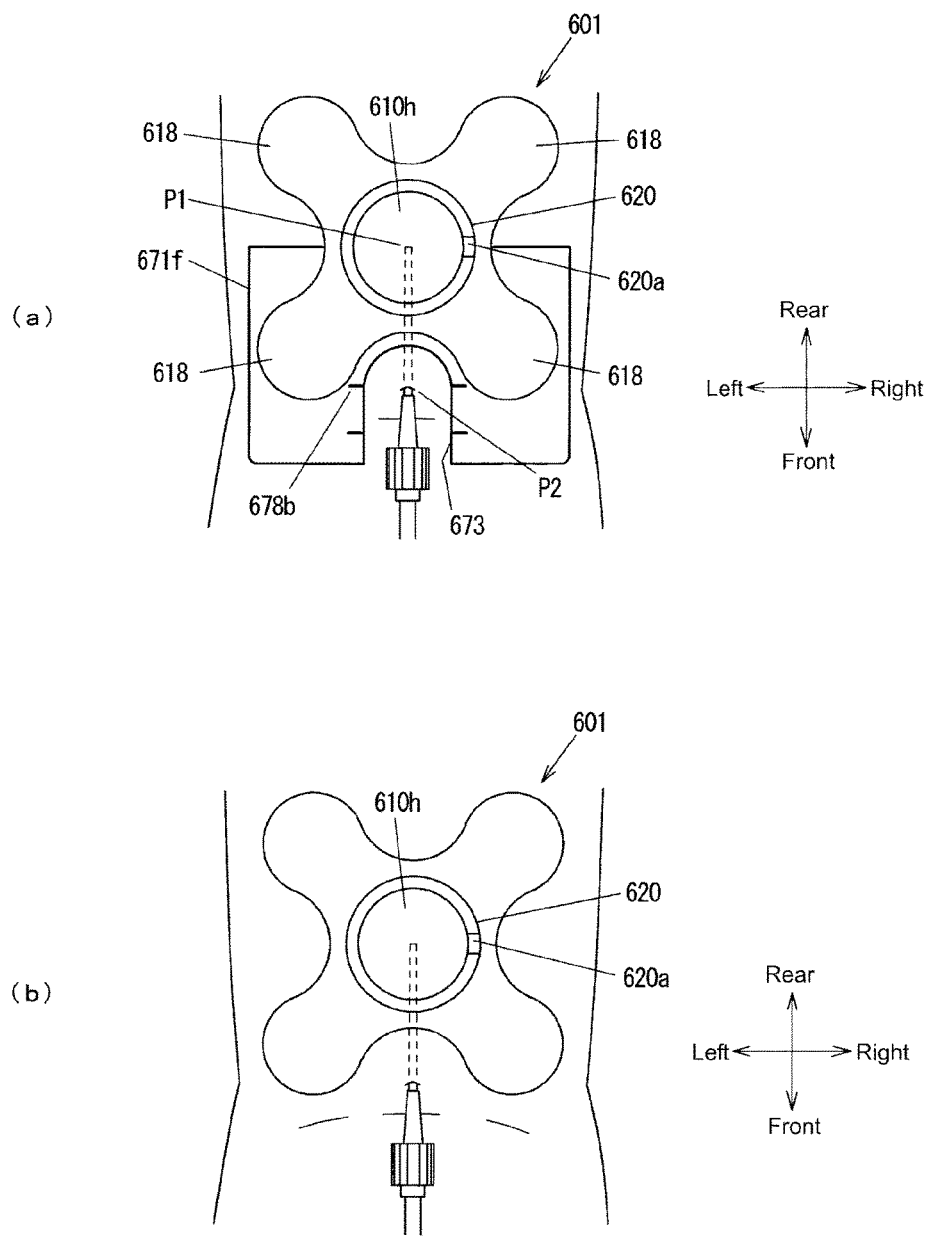
FIG. 19 is a plan view showing a procedure for attaching the sensor head.

The usage of such sensor pad kit 600 will be described below. FIG. 18 is a perspective view showing a final state of the sensor pad 601 attached to the patient's body. FIG. 19 is a schematic plan view illustrating a procedure of affixing the sensor pad 601. The procedure described below is only an example, and order of work procedure can be modified appropriately.

In FIG. 18 and FIG. 19, 'front' and 'rear' directions are shown, where, 'front' denotes a direction toward the palm of hand of the patient, and 'rear' denotes a direction opposite to the 'front' direction.

Firstly, as shown in FIG. 19(a), in a state of the injection needle (length 20 mm for example in this case) punctured into the patient's arm, the peelable film 671r is removed and half of the sensor pad 601 is to be attached to a predetermined position of the patient's arm. Specifically, the attaching is to be carried out upon positioning the sensor pad 601 such that a needle tip P1 of the injection needle comes to a center of the opening portion 610h of the sensor pad 601. A surrounding portion of an area of attaching may be cleaned before attaching.

The positioning can be carried out as described below. With regard to a frontward-rearward direction, by letting a proximal portion P2 of the injection needle and the gauge portion 678b (corresponding to 20 mm length), the needle tip P1 is positioned at the center of the opening portion 610h. Whereas, with regard to a leftward-rightward direction, by letting the injection needle to be a central portion in the leftward-rightward direction of the positioning recess 672, the needle tip P1 is positioned at the center (leftward-rightward direction) of the opening portion 610.

Next, the peelable film 671f at front side is to be removed, and a front half of the sensor pad 601 is to be attached. Accordingly, attaching of the sensor pad 601 as shown in FIG. 19B is finished. In the present embodiment, since four extended portions 618 are to be attached to the patient's body, it is possible to fix the sensor pad 601 favorably along the surface of the patient's body.

Thereafter, the sensor head 550 is to be installed from the upper side to the sensor holding portion 620. As mentioned above, at the time of inserting the sensor head 550 into the sensor holding portion 620, the sensor holding portion 620 is to be spread out elastically toward the outer side in the radial direction. As the sensor head 550 is moved up to a predetermined fixed position (refer to FIG. 16), the protrusion 621a is engaged with the portion of the sensor head (outer peripheral portion of the upper surface for example), and installation of the sensor head 550 is finished.

Here, in the present embodiment, since the cable 556 of the sensor is to be drawn in a direction (leftward-rightward direction in this case) different from the frontward-rearward direction, the injection needle and the cable 556 do not interfere by overlapping.

Thus, by a series of steps, the sensor pad 601 is attached to the patient's body and the sensor head 550 is installed.

When the treatment or examination is finished, the sensor pad 601 and the sensor head 550 are to be removed integrally from the patient's body. Or, after the sensor head 550 is removed first, the sensor pad 601 is to be removed from the patient's body. The injection needle may be removed after removing the sensor pad 601 or before removing the sensor pad 601.

According to the sensor pad kit 600 of the present embodiment described above, since positioning and fixing of the sensor head 550 is carried out by installing the sensor head 550 on the sensor holding portion 620 of the sensor pad 601, it is possible to carry out the job of installing the sensor head 550 easily. Besides, since the sensor holding portion 620 holds the housing by being deformed elastically, it is possible to hold the sensor head 550 stably.

Moreover, since the protrusion 621a of the inlet portion of the sensor holding portion 620 is engaged with the sensor head 550, it is possible to prevent the sensor head 550 from being removed during injecting a chemical liquid. According to the arrangement of the present embodiment in which the protrusion 621a is engaged with the sensor head 550, the user can check visually and/or by feeling by hand whether or not the sensor head 550 has been mounted correctly, thereby enabling to suppress the sensor head 550 from being installed wrongly.

Moreover, the sensor pad 601 of the present embodiment includes the plurality of (for example, four) extended portions 618, such method of fixing the pad by attaching the extended portions 618 is preferable from a point that it is possible to attach the pad favorably to a curved part (such as an arm) of patient's body.

Moreover, since the peelable film 671 has a structure of two separate films, there is an advantage that it is possible to attach the sensor pad temporarily in a state of the half of the film being removed.

Although the tip of the injection needle has already been punctured into the patient's body at the time of attaching the sensor pad 610, and a position of the tip cannot be checked, according to the present embodiment, by using the gauge portion 678a to 678c of the positioning recess 673, it is possible to determine accurately the position of attaching the sensor pad 610 with respect to the needle tip P1.

Second Embodiment

Figure 20:
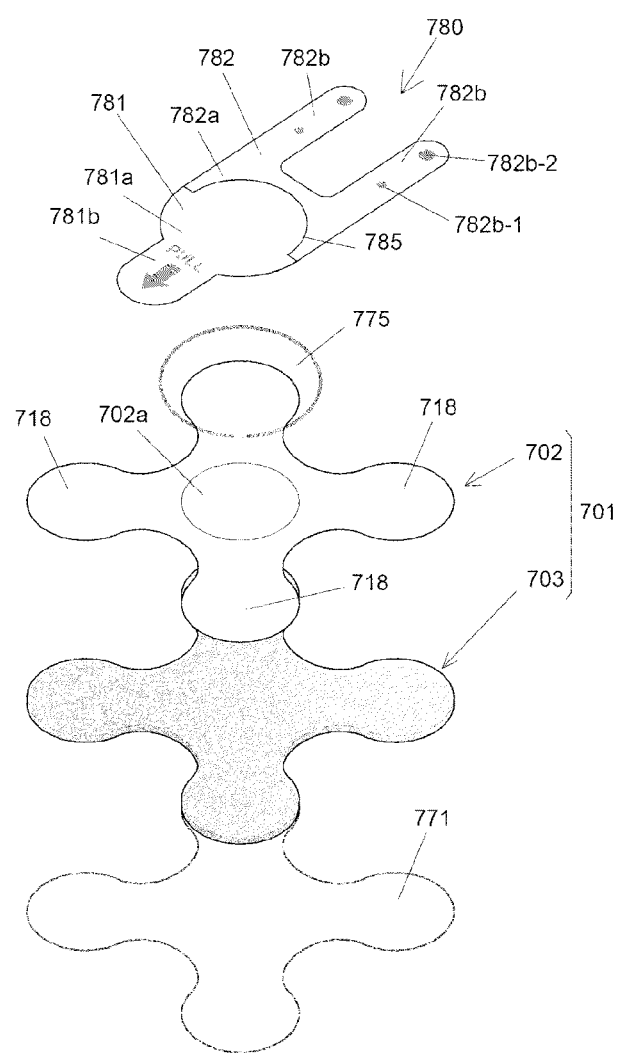
FIG. 20 is an exploded perspective view showing an arrangement of a sensor pad kit according to a second embodiment.

FIG. 20 is an exploded perspective view showing another example of the sensor pad kit.

The sensor pad kit includes a sensor pad 701 which is flexible, a peelable film 771 which is to be stuck to a lower surface of the sensor pad 701, an adhesive sheet 775 which is to be stuck to an upper surface of the sensor pad 701, and an upper peelable film 780 which is to be stuck to the adhesive sheet 775. It is not that all the members here are indispensable to the present invention.

The sensor pad 701 which is flexible has an arrangement in which a sheet substrate 702 made of a resin for example, and a gel pad 703 are stacked. A predetermined shape may be imparted to the sensor pad 701 by cutting a sheet having the two members stacked.

In the present embodiment, as an example, the sensor pad 701 may have a shape similar to the shape of the sensor pad 601 of the first embodiment. In other words, the sensor pad 701 may have four extended portions 718 extended radially toward an outer side from a central portion, and may have a cross shape (shape of an English alphabet X) as a whole.

The number of extended portions 718 may be two, three, or five or more. A shape of a tip side of the extended portion 718 may be a rectangular shape, or may be a substantial circular-arc shape as in the present embodiment. Specifically, the shape may be a semicircular shape or semielliptical shape. Moreover, it may be a polygonal shape where two tip angular portions of the rectangular shape are cut off obliquely.

All the extended portions 718 may have the same shape or each of the extended portion 718 may have a different shape. Moreover, the plurality of extended portions 718 may be divided into two or more than two groups, and extended portions belonging to one group may have a shape different from a shape of extended portions belonging to another group (for example, may be let to have different length, different thickness, or different shape of a tip portion).

The sheet substrate 702 may be made of a resin material such as PET (polyethylene) or may be made of paper. Moreover, a thickness of the sheet substrate 702 may be 0.05 mm or more, 0.1 mm or more, or 0.2 mm or more. The sheet substrate 702 may be colorless or may have been colored. It is preferable that the sheet substrate 702 has a light-transmitting property that does not hinder transmission of light irradiated from the sensor head 550 (refer to FIG. 11) and light reflected thereof. Such light-transmitting property may have been imparted to an area through which, light irradiated from the sensor head 550 and the reflected light thereof passes, and an area other than the light-transmitting area may not have light-transmitting property.

In an example in FIG. 20, the sheet 702 is a member without any opening portion formed therein. A circular portion denoted by reference numeral 702a in FIG. 20 at a substantially central portion of the sheet substrate 702 is not an opening portion, but a colorless transparent portion. This portion is a sensor holding portion 702a to which the sensor head 550 is to be attached. The sensor holding portion 702a may have a circular shape for example. The circular shape may be corresponding to the sensor surface 557 of the sensor head 550, same as the circular shape of the sensor surface, or larger than the circular shape of the sensor surface or smaller than the circular shape of the sensor surface.

As another aspect of the present embodiment, the portion 702a may be let to be an opening portion. The sensor holding portion 702a may be let to be a light-transmitting material allowing irradiated light from a sensor device to pass through, and not a colorless transparent portion. The sensor holding portion 702a may be let to be colored transparent portion for example.

Figure 23:
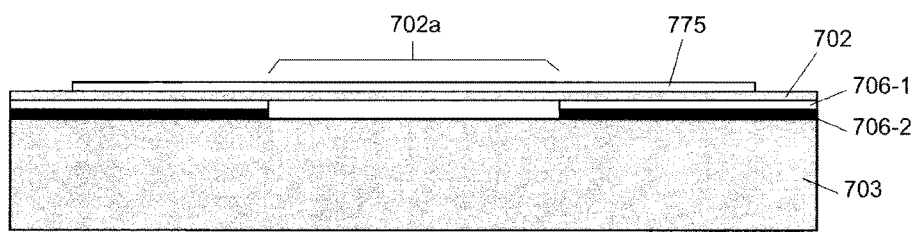
FIG. 23 is a cross-sectional view showing a cross section of the sensor pad kit in FIG. 20 (the peelable film is omitted)

The sheet substrate 702, as shown in FIG. 23, may be let to be light-shielding by forming at least one colored layer, excluding the sensor holding portion 702a (the entire light-shielding portion is not shown in FIG. 23 but a back surface of the extended portions 718 etc.) which is transparent. In this example, a first colored layer 706-1 and a second colored layer 706-2 are formed. As a matter of course, various colors can be selected, and as an example, the first colored layer 706-1 may be white and the second colored layer 706-2 may be black.

Figure 22:
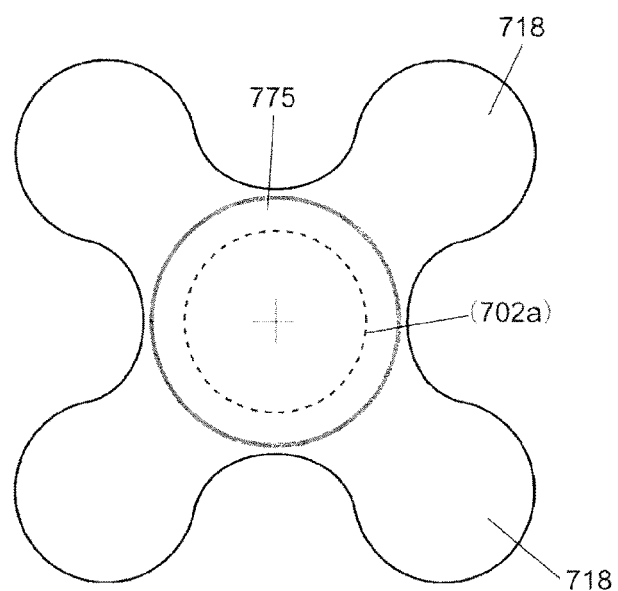
FIG. 22 is a plan view showing a state in which, an upper peelable film is removed from a state in FIG. 21.

As it is evident from FIG. 22 and FIG. 23, in the present embodiment, a light-shielding area exists at an outer side of the sensor holding portion 702a. The shape and size of the light-shielding area is not limited necessarily, and it is preferable that the light-shielding area exists in an area wider to some extent on the outer side of the sensor holding portion 702a (transparent portion) such that an adequate effect thereof is achieved. As an example, in a case in which, the sensor holding portion 702a is let to be circular, a circular area (concentric circles; excluding a central portion corresponding to the sensor holding portion 702a) of a diameter at least 1.1 times of a diameter of the circle, preferably 1.2 times of the diameter of the circle, and more preferably 1.3 times or more of the diameter of the circle may be the light-shielding area.

As the gel pad 703, as a specific example, products such as 'techno gel' (Sekisui Chemical Co., Ltd.) may be used. In other words, the gel pad 703 may be a sheet member of a soft material in which water, a moisturizing agent, and an electrolyte are retained in a hydrophilic three-dimensional polymer matrix. Since the gel pad 703 is a component to be stuck to a human body, it is preferable that the gel pad 703 does not have an effect on the human body when stuck thereto.

It is preferable that a thickness of the gel pad 703 is 0.1 mm or more and 0.3 mm or more, and 0.5 mm or more. Moreover, the thickness may be 0.7 mm or less, 1.0 mm or less, or 1.5 mm or less.

Moreover, it is preferable that a material for the gel pad 703 has an adhesive property of a degree that enables to stick as a single substance without using other fixing means (such as tape and band material) when the gel pad 703 is stuck to the patient. It is to be noted that the material does not hinder use of other fixing means in combination. The one or both of the surfaces of the gel pad 703 may have been provided with adhesive property.

The gel pad 703 may be any one of conductive or non-conductive. Silicone rubber may be used as the gel pad 703. The gel pad 703 may have even thickness throughout or the thickness may vary according to the location.

As shown in FIG. 20, in this example, no opening portion has been formed at the central portion (sensor holding portion in other words) of the gel pad 703. Consequently, in order to not to hinder transmission of irradiated light from the sensor head 550 (refer to FIG. 11) and light reflected thereof, it is necessary to be a material having a light-transmitting property. It may be any one of colorless and transparent. The entire gel pad 703 may be light transmitting or a portion which is light transmitting may have been formed partially.

The peelable film 771 is stuck to a lower surface of the gel pad 703. In this example, the peelable film 771 has a shape same as the shape of the gel pad 703. As another aspect, the peelable film 771 and the gel pad 703 may have different shapes, and various shapes such as a circular shape, a rectangular shape, and a polygonal shape can be used. The peelable film 771 may be one continuous film or may have been divided into two or more areas.

In the present embodiment, the sheet substrate 702 and the gel pad 703 are overlapped and let to be the sensor head 701. However, the sensor head 701 may be let to be single-layered or having a single member. Or, the sensor pad 701 may be let to be a multi-layered structure of three or more layers.

Next, a member on an upper side of the sheet substrate 702 will be described below. The adhesive sheet 775 to which the sensor surface of the sensor head 550 is to be attached is disposed on an upper surface of the sheet substrate 702. In this example, the adhesive sheet 775 is a double-stick tape having a circular shape slightly larger than the sensor holding portion 702a (refer to FIG. 22). As a matter of course, the shape of the adhesive sheet 775 is modifiable to various shapes, and may be any one of a triangular shape, a quadrilateral shape, a polygonal shape, an elliptical shape, and a shape in which these shapes are combined partially. The shape of the adhesive sheet 775 may be corresponding to the shape of the sensor surface of the sensor head. The adhesive sheet 775 may be colorless or may be colored, and it is preferable to be a material having a light-transmitting property for irradiated light from the sensor head 550 and reflected light thereof.

The adhesive sheet 775 may have at least an area through which the irradiated light from the sensor head 550 (refer to FIG. 11) and the reflected light thereof passes, opened. As an example, it may be a form (such as a ring shape) in which an opening portion is formed in a central portion. In a case of the adhesive sheet 775 having such opening area, the adhesive sheet 775 may not be light-transmitting necessarily.

The upper peelable film 780 is to be stuck on the adhesive sheet 775. The upper peelable film 780 may have any shape provided that the adhesive sheet 775 is covered. The upper peelable film 780 may have the same shape as the adhesive sheet 775. Paper or a resin material can be used as a material of the upper peelable film 780, and the material is not particularly limited.

In the present embodiment, the upper peelable film 780 can be divided into two portions 781 and 782 with a slit 785 having a substantially circular-arc shape as a boundary as shown in FIG. 20. A first portion 781 has a sticking portion 781a having a substantially circular shape to cover the sensor holding portion 702a and a tab 781b sticking out from an outer peripheral portion of the sticking portion 781a. The tab 781b is a portion that is to be pinched by the user at the time of removing the sheet.

The second portion 782 includes a sticking portion 782a that includes an area having a circular-arc shape to be stuck to a portion on an outer side of the sensor holding portion 702a, and two extended portions 782b and 782b mutually parallel that are extended in the same direction.

Figure 21:
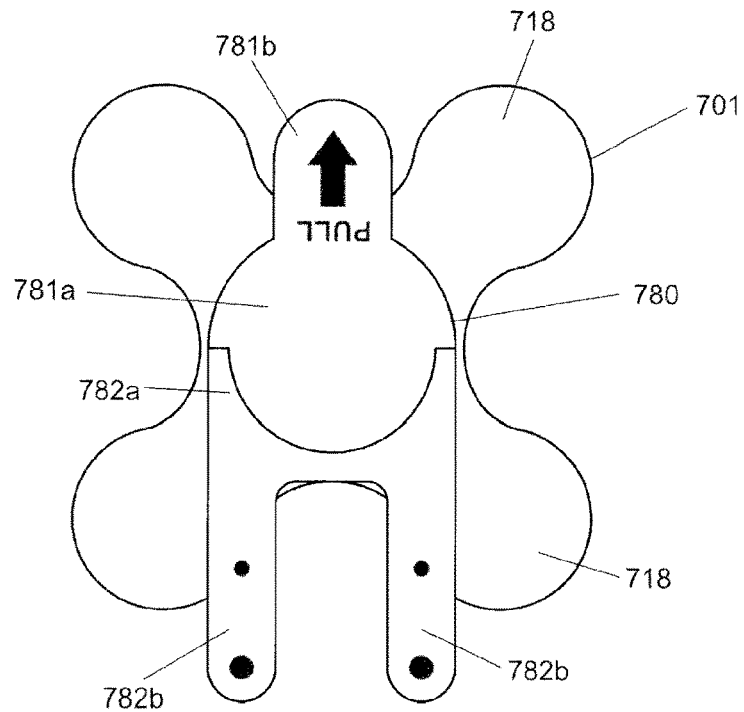
FIG. 21 is a plan view when the sensor pad kit in FIG. 20 is viewed from the top.

It is preferable that the tab 781b is extended toward an outer side of the sensor pad 701 as shown in FIG. 21. The two extended portions 782b and 782b also may be extended toward the outer side of the sensor pad 701.

Indicator portions 782b-1 and 782b-2 displaying a length from a predetermined reference position of the injection needle not shown (may be the proximal portion of the injection needle for example) up to the tip of the injection needle are displayed on each extended portion 782b. It is possible to stick the sensor pad 701 in a state of an approximate position of the needle tip of the injection needle by using the indicator portions 782b-1 and 782b-2. In this case, since it is possible to adjust a position of the center of the sensor holding portion of the sensor pad 701 with respect to the position of the needle tip of the injection needle that has been punctured, favorable leak detection by the sensor is possible.

The abovementioned sensor pad kit is used as described below as an example. Order of steps described below can be changed appropriately.

Firstly, in one example, the portion 781 of the upper peelable film 780 is removed, and an adhesive surface of the adhesive sheet 775 is to be exposed. Since the tab 781b has been formed, the first portion 781a can be removed easily.

Next, the sensor surface 557 (refer to FIG. 14 for example) of the sensor head 550 is to be stuck on the adhesive sheet 775. The cable 556 is to be installed to be directed substantially orthogonally to the extended portion 782b (this direction is also a direction substantially orthogonally to the patient's arm).

Next, after removing the peelable film 771 of the lower surface of the sensor pad 701, the sensor pad kit in a state of the sensor head 550 stuck is to be attached to the patient's arm. In this state, the second portion 782 of the upper peelable film 780 is remained as it had been.

The attaching, similarly as in the first embodiment, is to be carried out after the injection needle has been punctured. Before attaching, the portion surrounding the position of attaching is to be cleaned according to the requirement. Here, since tip side of the injection needle is inserted into the body of a patient and an accurate position thereof cannot be observed visually, it may be difficult to attach the sensor pad kit to an intended position (a position at which, the center of the sensor head coincides with the needle tip).

Therefore, in the present embodiment, the extended portions 782b and 782b of the upper peelable film 780 are to be used. Specifically, positioning is to be carried out by letting the indicator portion 782b-1 or 782b-2 displayed on the extended portions 782b and 782b coincide with a predetermined reference position of the injection needle (similarly as in the first embodiment). Accordingly, it is possible to adjust the position of the needle tip position and the center of the sensor head.

By sticking the four extended portions 718 of the sensor pad 701 firmly (as a specific example, two of the four extended portions 718 are stuck to a forearm side and the remaining four of the four extended portions 718 are stuck to an upper-arm side), the sensor pad 701 and the sensor head 555 are fixed stably.

Thereafter, the second portion 782 of the remaining upper peelable film 780 is to be removed.

According to the sensor pad kit described above, since the sensor pad 701 is attached to the patient's body by using the four extended portions of the sensor pad 701, it is possible to attach stably. Besides, since such sensor pad 70 follows the movement of the patient favorably and does not come off even in a case such as when the patient has bent the arm, a portion of the sensor pad 701 is prevented from coming off due to the movement of the patient during the examination, and accordingly preventing a situation in which the detection of leak of a chemical liquid cannot be carried out.

Moreover, according to the present embodiment, since at least a single-layered member (here, the gel pad 703, the sheet substrate 702, and the adhesive sheet 775) is interposed between the sensor head 550 and the surface of the patient's body thereby the sensor head 550 not making a direct contact with the surface of the patient's body, it is hygienic.

Moreover, in a case in which, the sensor pad 701 has a light-shielding layer (706-2), since light is prevented from entering from outside into a light-receiving portion of the sensor head 555, it is possible to continue the desired leak detection. Particularly, in the present embodiment, since the outer side of the circular-shaped sensor holding portion 702a is the light-shielding area, in this area, light from the outside cannot enter the light-receiving portion of the sensor head 550 upon transmitting through the gel pad 703.

Although the present invention has been described above specifically, the following modifications may be made in the sensor pad kit.

(d1) The protrusion 621a of the sensor holding portion 620 is to be omitted, and the sensor head 550 is let to be held by being press-fitted into the sensor holding portion 620. In this case, an inner diameter of the sensor holding portion 620 may be set to be somewhat smaller than an outer diameter of the sensor head 550.

(d2) The sensor head 620 is arranged such that a plurality of types of sensor heads of different sizes can be installed.

(d3) To fix the sensor head 620 more reliably, a fixing tape is to be stuck further to cover the sensor head 620.

(d4) An indicator for carrying out adjustment of position of the injection needle in the leftward-rightward direction (refer to FIG. 19) has been displayed on the peelable film 671*f* and/or 671*r*. The indicator may be in the form of a straight line along the needle tip shown by dashed lines in FIG. 19(*a*) for example.

(d5) Two or three or more than three recesses 620*a* for drawing the sensor cable are to be formed. For instance, the two recesses 620*a* may be disposed at intervals of 180° mutually, thereby improving the degree of freedom of disposing the cable.

The following modifications may be made in the embodiment in FIG. 20.

(e1) The number of extended portions 782*b* of the upper peelable film is let to be one and not two.

(e2) The number of the indicator portions 782*b*-1 and 782*b*-2 on the extended portion 782*b* is let to be three or more, or an arrangement is to be made such that a numerical value indicating the length up to the needle tip is also indicated.

The following modifications may have been made in the embodiment in FIG. 23.

(e3) An opening portion (opening portion of an area facing the sensor surface of the sensor head) is to be provided to all or at least two of the adhesive tape 775, the sheet substrate 702, and the gel pad 703. In a case of providing the opening portion to all the members, another protective film (not shown) may be interposed so that the sensor head 550 does not make a direct contact with skin.

(e4) Printing (706-1 and 706-2) is to be carried out on the upper surface of the sheet substrate 702.

Third Embodiment

Figure 24:
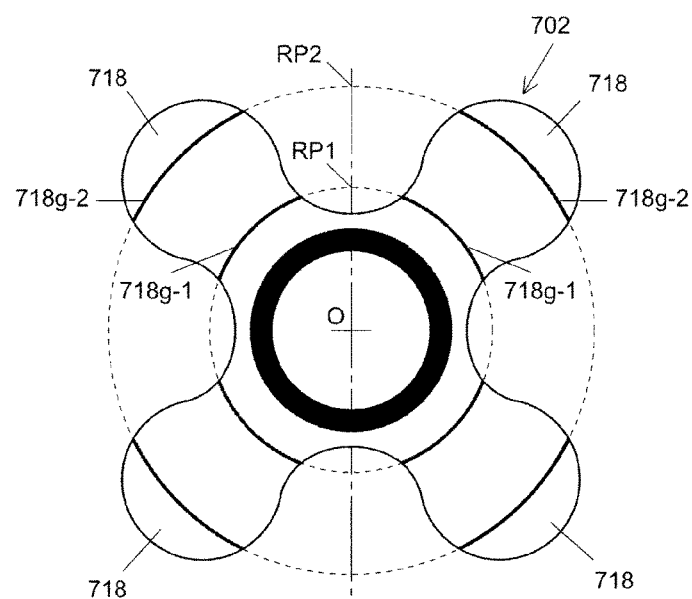
FIG. 24 is a plan view showing an example of a sensor pad according to still another embodiment.
Figure 25:
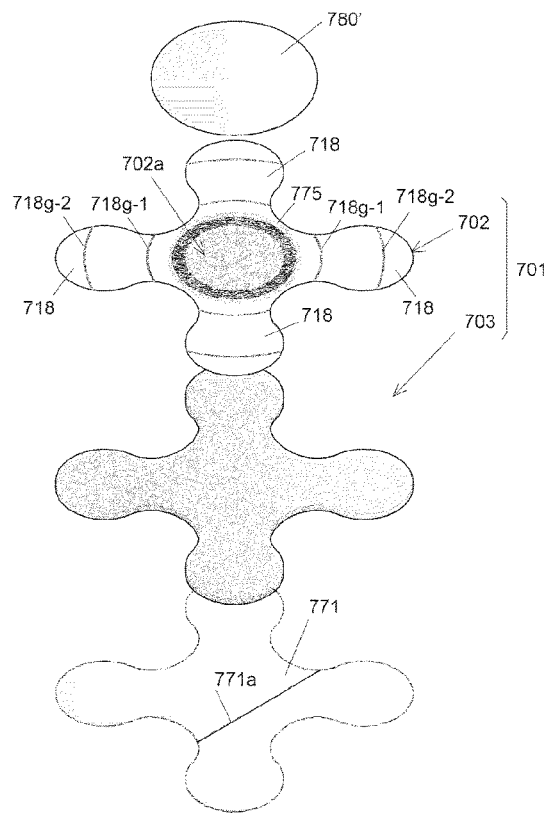
FIG. 25 is an exploded perspective view of a sensor pad kit according to still another embodiment.
Figure 26A:
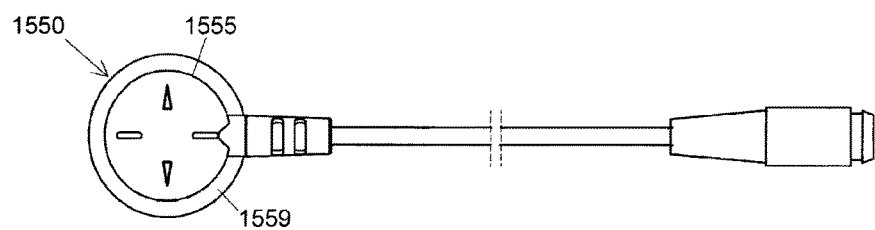
FIG. 26A is a plan view of a sensor head according to still another embodiment.
Figure 26B:
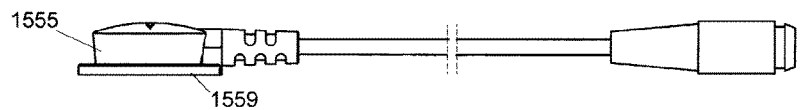
FIG. 26B is a front view of the same sensor head, and a rear view is to be indicated to be symmetrical to the front view.
Figure 26C:
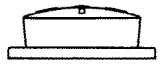
FIG. 26C is a left-side-surface view of the same sensor head.
Figure 26D:
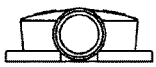
FIG. 26D is a right-side-surface view of the same sensor head.
Figure 26E:
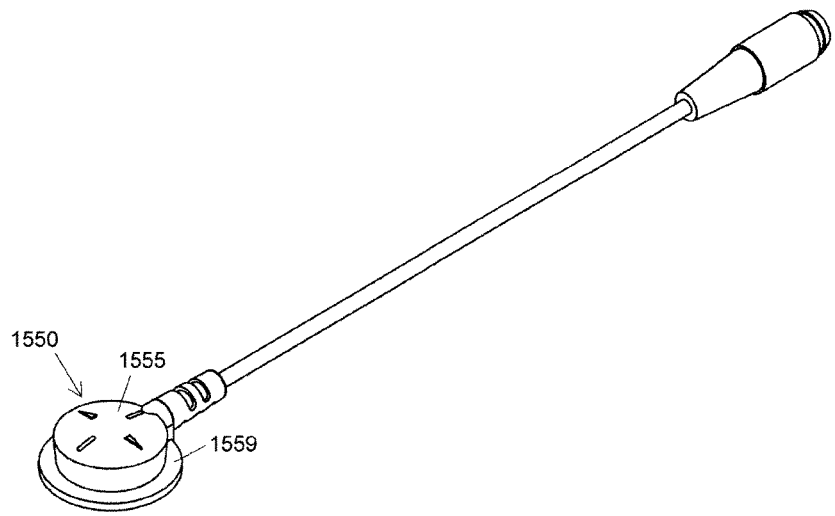
FIG. 26E is an upper-surface side perspective view of the same sensor head.
Figure 26F:
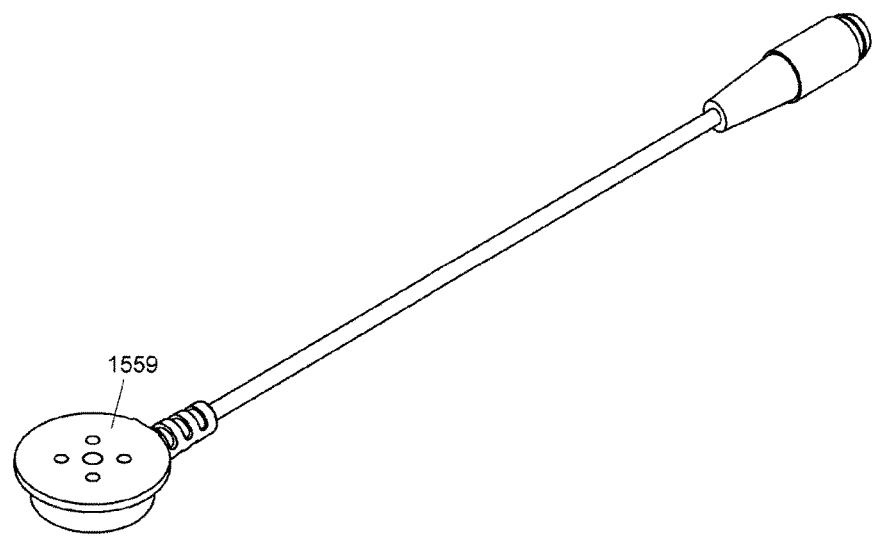
FIG. 26F is an lower-surface side perspective view of the same sensor head.

FIG. 24 and FIG. 25 show another example of a sensor pad kit. The basic arrangement is similar as in the second embodiment, but it differs at the following points:

Shape of an upper peelable film 780'

Guide lines 718*g*-1 and 718*g*-2 on the upper surface of the sheet substrate 702

Peelable sheet 771 that can be divided

Repetitive description of structures same as or substantially same as in the embodiments described above will be omitted.

As shown in FIG. 25, in this example, the upper peelable film 780' is formed to be circular-shaped. As a matter of course, a protrusion (tab) which is not shown may be formed on a portion of an outer peripheral portion of the upper peelable film 780' such that the user can remove the film by pinching this portion. The upper peelable film 780' may be one continuous sheet which is not divided or maybe two or more than two sheet materials that can be divided. The upper peelable film 780' may have any shape in addition to the circular shape, such as an elliptical shape, a polygonal shape, a rectangular shape, or a combination of these shapes.

Referring to FIG. 24, the guide lines 718*g*-1 and 718*g*-2 having a circular-arc shape are indicated on the upper surface of the sheet substrate 702 of the present embodiment. The guide line 718*g*-1 corresponds to a reference circle (indicated by dashed lines) having a relatively small diameter, and the guide line 718*g*-2 corresponds to a reference circle having a relatively large diameter.

Firstly, to explain the guide lines 718*g*-1 as an example, the guide lines 718*g*-1 are indicated such that a distance between an intersection point RP1 of the reference circle having a small diameter indicated by the dashed lines and a center O corresponds to a distance from a predetermined reference position of the injection needle (P2 in the example in FIG. 19) up to the needle tip position P1.

In other words, a position of the guide line 718*g*-2 has been set to be such that when the position adjustment of the intersection point RP1 and the reference position P2 of the injection needle P2 (refer to FIG. 19) is carried out, the needle tip position P1 is within a circle of a predetermined radius having the center O as a center. The 'circle of a predetermined radius having the center O as a center' means that may be let to a size same as the sensor surface 557 (circular shape) of the sensor head 550, or a size somewhat smaller than that of the sensor surface 557, or a size somewhat larger than that of the sensor surface 557.

The injection needle corresponding to the guide lines 718*g*-1, as an example, may be an injection needle having a length from the reference position P2 of the proximal position of the needle up to the needle tip position P1 of about 14 mm to 25 mm.

Regarding the guide lines 718*g*-2 of larger diameter, similarly as the guide lines of smaller diameter, the guide lines 718*g*-2 are indicated such that a distance between a intersection point RP2 of the reference having a large diameter corresponding to the guide line 718*g*-2 and the center O corresponds to a distance from a predetermined reference position of the longer injection needle (P2 in the example in FIG. 19) up to the needle tip position P1. For instance, the injection needle corresponding to the guide lines 718*g*-2, as an example, may be an injection needle having a length from the reference position P2 of the root of the needle up to the needle tip position P1 of about 30 mm to 45 mm.

By such guide lines 718*g*-1 and 718*g*-2, at the time of attaching the sensor pad 701 to the patient's body, by determining an approximate position of the intersection point RP1 by the user while referring to the indicator of the pair of adjacent guide lines 718*g*-1 and 718*g*-1, and adjusting the position of the intersection point and the reference position P2 of the injection needle (already punctured into the patient's body at this point of time), it is possible to stick the sheet substrate 702 to an appropriate position. Here, the 'appropriate position' refers to a position where the needle tip position P1 (refer to FIG. 19) is at an inner side of a circle of the sensor holding portion 702*a*.

In the example in FIG. 24 and FIG. 25, although two types of guide lines having a large diameter and a small diameter have been printed, the guide lines may be let to be of only one type according to the number of types of injection needle, or may be of three or more than three types. Moreover, a numerical indicator indicating the length of the corresponding needle may have been added near the guide lines 718*g*-1 and 718*g*-2.

Regarding the guide lines 718*g*-1 and 718*g*-2, colors of the lines may be same or may be different. Moreover, a line width may be the same or may be different.

In this example, moreover, the peelable sheets 771 can be removed separately, one by one, on two sides of a parting line 771*a*. A position of the parting line 771*a* may be on a center line of the peelable sheet 771 or may be offset from the center line of the peelable sheet 771 (FIG. 25).

As the usage of the abovementioned sensor pad, firstly, the upper peelable film 780' is to be removed and the sensor head (not shown) is to be fixed by attaching to the sensor pad 701. Next, with the sensor pad 701 in this state, the peelable sheet 771 on the lower-surface side is to be removed one by one, and after carrying out the position adjustment of the sensor pad 701 while checking the guide lines 718*g*-1 and 718*g*-2, the sensor pad 701 is to be attached to the patient's body. As a matter of course, after attaching the sensor pad 701 to the patient's body, the sensor head may be fixed by removing the upper peelable film 780'.

By the sensor pad kit according to the present embodiment described above, it is possible to attach the sensor head 550 (refer to FIG. 14 for example) to the patient's body by a simple procedure. Particularly, since the four extended portions 718 of the sensor pad 701 are to be stuck along the body, stable fixing is realized. For instance, since each extended portion 718 follows the movement and does not come off easily even in a case such as when the patient has bent the arm, it is possible to prevent defective leak detection due to the sensor pad coming off.

Furthermore, according to the present embodiment, since at least one layer (here, the gel pad 703, the sheet substrate 702, and the adhesive sheet 775) is interposed between the sensor pad 550 and the surface of the patient's body thereby the sensor head 550 not making a direct contact with the surface of the patient's body, it is hygienic.

Moreover, matters which are common in the other embodiments as well, as it is evident from FIG. 24, it is preferable in one aspect that the sensor pad is formed symmetrically about a predetermined center line (a center line extended in a longitudinal direction in FIG. 24). The reason being that, after the use, the process of removing the sensor pad from the patient's body, and removing the sensor head from the sensor pad (specifically, the upper surface of the sheet substrate 702) can be carried out hygienically. In other words, in a state of the sensor head attached to the sheet substrate, the user rolls the sensor pad such that adhesive layers of the extended portions 718 on the left and right (two extended portions at lower right and lower left in FIG. 24 for example) abut mutually. Accordingly, the upper surface of the sensor pad becomes a curved surface, and it is easy to remove the sensor pad. Incidentally, in a state of the sensor head removed from the patient, blood etc. might be adhered to the back surface of the sensor pad. The user touches the blood unknowingly, it is not desirable hygienically. However, in a case of the line-symmetric shape as in the present embodiment, the portions on left and right having the same shape can be pressed by finger from the upper-surface side of the pad and stuck mutually, thereby making it possible to carry out the job hygienically.
Sensor Head According to Still Another Embodiment)

A sensor head 1550 having a shape of a housing as shown in FIG. 26A to FIG. 26F may be used. The sensor head 1550, basically, has an outer shape similar to the shape in FIG. 11 to FIG. 14, but differs at a point that a flange portion 1559 is formed. Since light-emitting elements and a light-receiving element can be let to be similar as in the abovementioned sensor head, the repetitive description thereof will be omitted, and only structural components that differ will be described.

The sensor head 1550 includes a housing 1555 and the flange portion 1559 formed at a bottom-surface portion of the housing 1555. The flange portion 1559 may have any shape, and the shape may be a polygonal shape such as a quadrilateral shape, a hexagonal shape, and octagonal shape, or may be a circular shape or an elliptical shape for example, and in this example the shape of the flange portion 1559 is a circular shape. A lower surface of the flange portion 1559 may be such that an adhesive sheet 775 (refer to FIG. 25) as mentioned above is to be stuck. Although the lower surface of the flange portion 1559 in this example is a flat surface, it is not limited to this, and may be let to be a curved surface in some cases (a gently curved surface along a curve of the patient's arm for example, more specifically, circular-arc surface).

In a case of such sensor head 1550 having the flange portion 1559 formed, since an area that makes contact with the adhesive sheet 775 (an example) is larger as compared to a sensor head of a type without the flange portion 1559, it is possible to carry out the fixing more stably. Moreover, at the time of using the sensor head 1550, (in other words, in a state of the sensor head 1550 attached to the patient's body), since light from the outside cannot enter easily into a lower-surface side of the flange portion 1559, it is possible to reduce occurrence of defective detection caused due to light from the outside.

An indicator portion (a protrusion or a recess) such as an arrow formed on an upper surface of the sensor head 1550 may have been formed or may not have been formed. The length of the cable can be set freely. The present application also discloses a partial design of only a housing portion of the sensor head. More specifically, the present application also discloses a partial design of only the sensor surface (the bottom surface of the flange portion 1559 for example).

Still Another Embodiment

Figure 27:
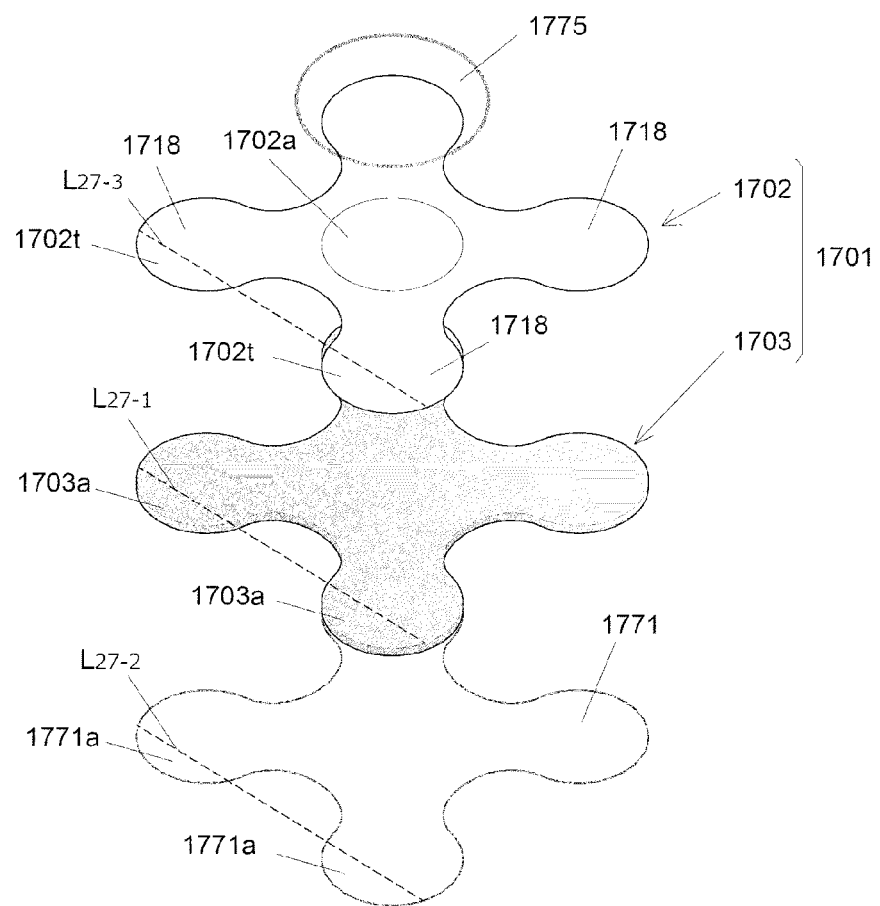
FIG. 27 is an exploded perspective view of a sensor pad kit according to still another embodiment.

FIG. 27 is an exploded perspective view of a sensor pad kit according to one aspect of the present invention. As shown in the diagram, the sensor pad kit includes a sensor pad 1701, a peelable film 1771 to be stuck to a lower surface of the sensor pad 1701, and an adhesive sheet 1775 to be stuck to an upper surface of the sensor pad 1701. It is not shown in the diagram but the sensor pad 1701 may include a peelable sheet on the adhesive sheet 1775.

Since a material, an arrangement and a shape of the sensor pad 1701 can be let to be basically similar as in the abovementioned embodiments, description in detail thereof will be omitted. The sensor pad 1701 is a stacked body of a sheet substrate 1702 and a gel pad 1703. Both surfaces of the gel pad 1703 may be adhesive. In the present specification, the overall gel pad sometimes is also referred to as 'adhesive layer'. One surface of the gel pad 1703 is to be adhered to the sheet substrate 1702. The sheet substrate 1702 and the gel pad 1703 basically have the same shape (described below in detail).

The whole of gel pad 1703 may be made of a light-transmitting material. Or, the gel pad 1703 may be partially made of a light-transmitting material.

The sheet substrate 1702 may have a layered structure as shown in FIG. 23. The sheet substrate 1702 may have a light-transmitting area (refer to reference numeral 1702) and at least one extended portion 1718 extending from the light-transmitting area toward an outer side. Area other than the area of reference numeral 1702 may be let to be an area which is not light-transmitting. A sensor device is disposed in the area of reference numeral 1702. The adhesive sheet 1775 for fixing the sensor device is to be stuck on the sheet substrate 1702. For details of each member, refer to the description of the abovementioned embodiments.

In the example in FIG. 27, a portion of the gel pad 1703 may have been cut off. Specifically, a tip portion 1703a of an extended portion of the gel pad 1703 may have been cut off with a straight line $L_{27-1}$ as a reference. As a matter of course, a part of not two extended portions, but of one extended portion or three or more than three extended portions may have been cut off. The portion may be cut off with a line of any shape as a reference and not with a straight line as a reference.

Similarly, for the peelable film 1771, a tip portion 1771a of an extended portion may be cut off with a straight line $L_{27-2}$ (for example) as a reference. A shape of the peelable film 1771 and a shape of the gel pad 1703 may be the same.

Whereas, according to one aspect, it is preferable that the sheet substrate 1702 has an extended portion (1702t) which is extended beyond a straight line $L_{27-3}$. To put in other words, this portion of the sheet substrate 1702 is a non-adhesive portion 1702t which is not provided with an adhesive layer on a back surface. A size of the non-adhesive portion 1702t is not limited in particular, and according to one aspect, it is preferable that an area of the non-adhesive portion 1702t is such that it can be pinched by fingers.

In the present embodiment, in a case in which, the non-adhesive portion 1702t has been provided, the non-adhesive portion 1702t is extended out through the cut-off portion of the gel pad 1703 at the time of using the sensor pad 1701. Consequently, after the use, since it is possible to remove the pad from the patient's body while pinching the non-adhesive portion 1702t by fingers, the process can be carried out easily.

Figure 28:
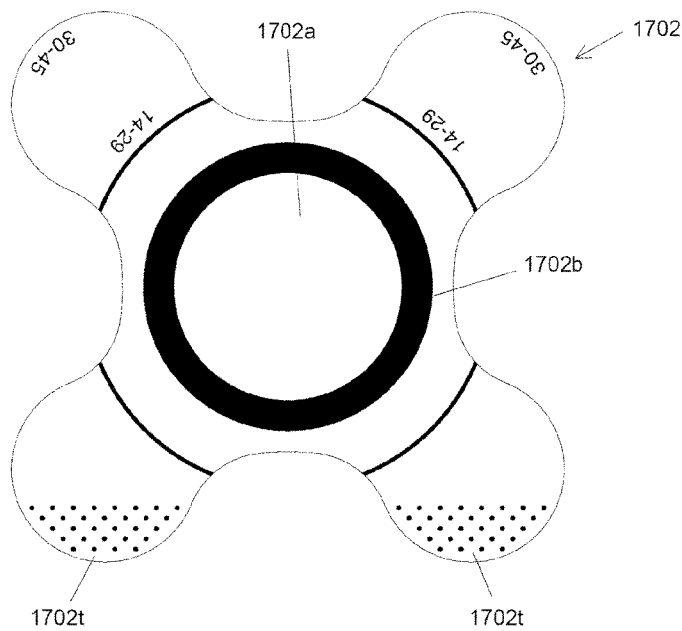
FIG. 28 is a diagram showing an example of a display on a sheet substrate.
Figure 29:
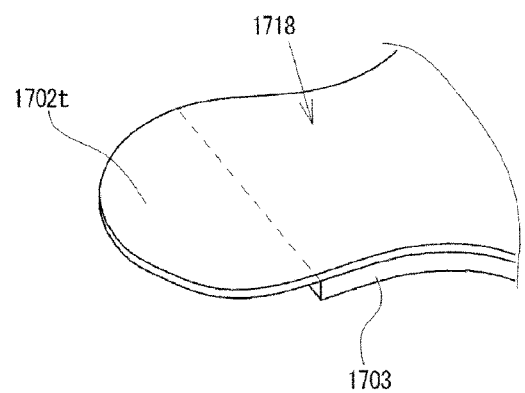
FIG. 29 is a perspective view showing partly enlarged the sensor pad.

Printing may have been or may not have been carried out on a front surface of the sheet substrate 1702. FIG. 28 is an example of the sheet substrate 1702 subjected to printing.

Although it is not limited, a predetermined color, design, and/or hue may have been applied to a location of the non-adhesive portion 1702t. In this example, a design of dots has been indicated. By such display of the non-adhesive portion 1702t, it is easy for the user to identify the extended portion visually.

In a case in which, the circular-arc shaped guide lines indicating the length of the needle have been printed on the sheet substrate 1702 as described by referring to FIG. 24, a number indicating the needle length may have been indicated near the guide line. In this example, '14-29' means that the needle length is 14 mm to 29 mm. A numerical value of the needle length more than this ('30-45' in this example) may have been indicated.

A guide portion 1702b for fitting, which is colored and surrounds the sensor holding portion 1702a (light-transmitting portion) may have been printed. The guide portion 1702b has a shape corresponding to the sensor head. Specifically, in this example, the guide portion 1702b is indicated as a ring having an outer shape same as the outer shape of the sensor head (for example, the flange portion 1559 of the device in FIG. 26A). In a case in which, a guide portion for fitting having a shape corresponding to the outer shape of the sensor head has been printed in such manner, since it is possible to attach the sensor head with reference to the guide portion for fitting, it is possible to reduce occurrence of mistaken fixing at the time of use, thereby making it advantageous.

(Supplementary Explanation of Peelable Film)

The peelable film 1771 in FIG. 27, as a matter of course, may be a film divided into two or into three or more. A parting line in this case (corresponds to the parting line 771a in FIG. 25) may be parallel or substantially parallel to the straight line $L_{27-1}$ for example.

The following idea may have been devised further in an arrangement of dividing the peelable film 771 into two as in FIG. 25. Out of the peelable film divided into two, one having a large size is let to be a first peelable film and the other having a small size is let to be a second peelable film. In this case, the first peelable film may have been formed such that even when the second peelable film is released, an adhesive layer on the back surface of the sensor holding portion (refer to 702a and 1702a. A light-transmitting portion on which the sensor head is disposed) being covered by the first peelable film, is not exposed. According to such arrangement, since the adhesive layer on the back surface of the sensor holding portion is maintained to be hygienic, the safety is further secured. Moreover, if fingerprints are left behind on the adhesive layer on the back surface of the sensor holding portion, there is a possibility of having an adverse effect on the detection accuracy. However, according the present embodiment, it is possible to prevent an occurrence of such problem.

In the description above, although it was assumed that the peelable film is divided into two, the peelable film may have been divided into three as a matter of course. According to one aspect of the present invention, the first peelable film covering the sensor holding portion need not be necessarily larger than the other peelable film. This is because there may be a case in which, the size of the first peelable film covering the sensor holding portion is smaller than the other peelable film according to the mode of division.

(Example of Specific Arrangement of Gel Pad)

Figure 30:
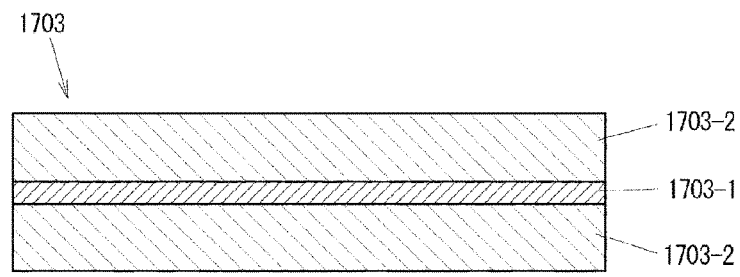
FIG. 30 is a cross-sectional view showing an example of layer arrangement in a gel pad.

The gel pad (703 and 1703) may have a layer arrangement as shown in FIG. 30. In this example, the gel pad 1703 may include a base layer 1703-1 as a core, and adhesive gel layers 1703-2 formed on two sides of the base layer 1703-1. According to one aspect, it is preferable that each layer is made of a light-transmitting material. The base layer 1703-1 may have been formed of a fibrous material such as a nonwoven fabric. An overall layer-thickness of the gel pad 1703 may be about 0.3 mm to 2.0 mm for example, and may be about 0.5 mm to 1.5 mm preferably.

(Specific Example of Leak Detection System)

Figure 31:
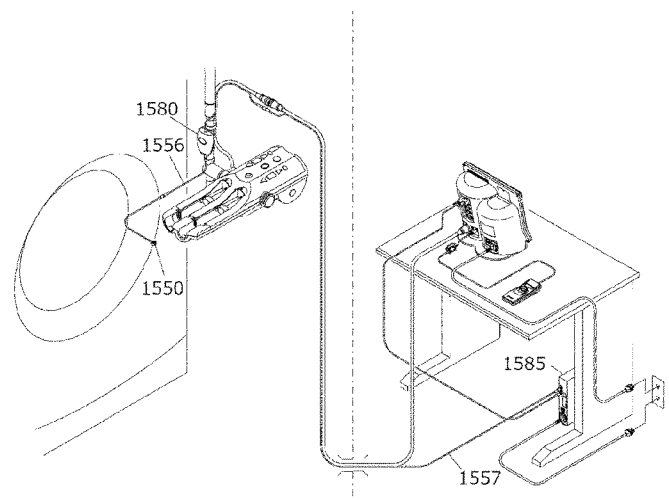
FIG. 31 is a perspective view showing an example of a leak detection system.

A leak detection system may include the sensor head 1550, an operation unit 1580, and a substrate module 1585 as shown in FIG. 31.

As the sensor head 1550, the abovementioned head can be used in one example. The sensor head 1550 may be connected to the operation unit 1580 via a cable 1556.

The operation unit 1580 has one or a plurality of buttons. In this example, one physical button 1581 is disposed on the housing 1583. The physical button 1581 may be a button that can emit light. Specifically, the physical button 1581 may have a light-emitting portion inside which emits light when the switch is pushed, or a color of light emitted or a pattern of light emitted is changed when the switch is pushed. As a matter of course, two or more than two buttons that emit light, may be provided to the housing 1583. A light source of the light-emitting portion may be an LED. The housing 1583 may have a structure that is attached to the injection head, or may have a structure that is attached to a movable stand or an arm suspended from the ceiling. The power source need not be necessarily inside the button, and one or a plurality of light-emitting portions may have been disposed separately, independent of the button.

The substrate module 1585 includes a housing and an electric circuit built-in therein, and is electrically connected to the operation unit 1580 and the sensor head 1550. The circuit of the substrate module 1585 may be the circuit shown in the example in FIG. 5. Such electric circuit may be connected via the interface of the console (refer to FIG. 3), and may carry out an exchange of electric signals with the control section 153 of the same console.

The substrate module 1585 may be supplied with an electric power from a commercial power supply. Or, the substrate module 1585 may be supplied with an electric power from a console etc. Or, the substrate module 1585 may be of a portable type having a built-in battery.

An example of an operation of such leak detection system will be described below.

Firstly, the sensor head and the gel pad are to be fixed to the patient's body by the procedure that has already been described.

The operator pushes the button 1581 on the operation unit 1580. Accordingly, the electric circuit of the substrate module 1585 (or another electric circuit of the chemical liquid injection apparatus) starts the leak detection. The electric circuit (or another electric circuit of the chemical liquid injection apparatus), in response to this, causes the button 1581 to emit light.

Although it has not been limited, in a case in which, the leak detection has started, a display (such as a graphic image) indicating that the leak detection has started may be displayed on a predetermined display. Such graphical image as an alarm display may be displayed in any image of a graphical user interface that may be displayed in the chemical liquid injection system of the present embodiment. It may be displayed as a graphical image for setting conditions, a graphical image during injecting, or a portion of a graphical image showing an injection result. The timing of display is not limited to the main injection and may be displayed at the time of pre-injection.

The electric circuit of the substrate module (or another electric circuit of the chemical liquid injection apparatus) may carry out an operation of calibration of the sensor at the time of start of detection. Moreover, it may also carry out an operation of determining whether the sensor head has been attached correctly.

In a case in which, accordingly, it has been determined that the sensor head is not attached correctly or has come off, an alarm display and/or an alarm sound may be generated. Specifically, the color of the light-emitting portion may be changed, or switching between lighting up and blinking may be carried out. A buzzer or a speaker may have been built-in, and the alarm sound may be generated.

Some of the specific examples of operation that may be used in the present system will be described below, but the present invention is not limited to the examples described below:

When an extravascular leak has been detected, an alarm sound is generated from a buzzer or a speaker.

When an extravascular leak has been detected, a color of the light-emitting portion is changed (to red color for example).

When an extravascular leak has been detected, a graphical image (as an example, a color, a shape, and a light emission pattern same as at least one of the color, the shape, and the emission pattern of the light-emitting portion of the operation unit) indicating that the extravascular leak has been detected is displayed on a display of the chemical liquid injection apparatus or another display connected thereto.

During detection of an extravascular leak, the detection is stopped or terminated by pressing the button 1581 on the operation unit 1580.

Without carrying out an operation of stopping or terminating, when the sensor head has been removed, an alarm display and/or an alarm sound is generated.

Figure 32:
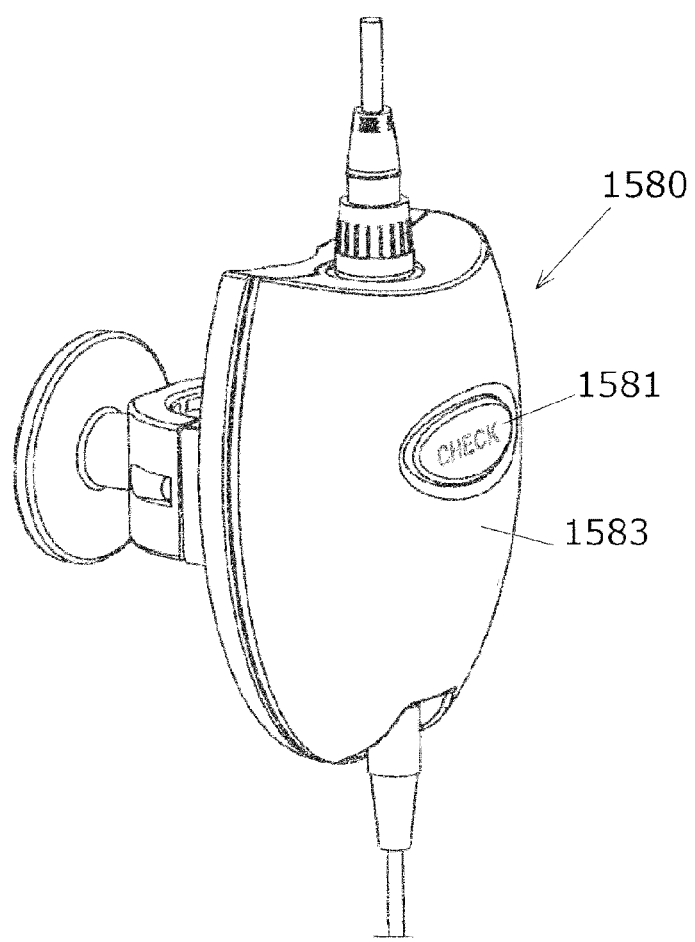
FIG. 32 is a perspective view showing one of components of the leak detection system.

According to FIG. 31 and FIG. 32, since the operation unit 1580 is positioned near the injection head, the operator can start or stop the operation of leak detection near the patient, thereby leading to favorable workability. Moreover, since the light emission of the button of the operation unit 1580 and/or sound become an alarm, the operator is susceptible to notice abnormality, which is preferable from a viewpoint of the safety of examination.

(Note A)

The present application discloses the following invention:
1. A sensor pad kit (600) includes
    a sensor pad (601) having a flexible base member (610) in the form of a sheet on which, an adhesive surface (610*b*) to be attached to patient's body has been formed, and a sensor holding portion (620) on which a sensor device (550) formed on a portion of the flexible base member (610) is removably mounted, and
    a peelable film (670) which is attached to the adhesive surface (610*b*) of the sensor pad (601), wherein
    the sensor holding portion (620) is made of an elastic material, and holds the device by elastic deformation when the sensor device (550) is attached.
2. The sensor pad kit, wherein the sensor holding portion (620) is formed to be frame-shaped or cylinder shaped in accordance with the sensor device, to be capable of holding a side-wall portion (555*c*) of the sensor device.
3. The sensor pad kit, wherein a protrusion (621*a*) which is to be engaged with a portion of the sensor device when the sensor device is moved up to a predetermined position, is formed on an inlet portion of the sensor holding portion (620).
4. The sensor pad kit, wherein a recess (620) for allowing a cable of the sensor device to pass is formed in the sensor holding portion (620).
5. The sensor pad kit, wherein the base member (610) has a plurality of extended portions (618) extended toward an outer side from a central portion in a plan view.
6. The sensor pad kit, wherein the number of extended portions (618) is four.
7. The sensor pad kit, wherein the base member 610 has an opening portion (610*h*) at a part (site) where a sensor surface (557) of the sensor device is positioned.
8. The sensor pad kit, wherein a light-shielding wall (621*b*) which surrounds an outer periphery of the opening portion (610*h*) is formed on a back surface of the base member (610).
9. The sensor pad kit, wherein the peelable film (671) is divided into at least two.
10. The sensor pad kit, wherein a positioning recess (673) which includes a indicator portion displaying a length from a predetermined reference position of the injection needle up to a tip of the injection needle is formed in the peelable film (671).
11. The sensor pad kit, wherein a plurality of positioning recesses (673) is formed.
12. The sensor pad kit, wherein a material of a layer forming the adhesive surface (610*b*) is silicone rubber.
13. The sensor pad kit further includes a packaging bag which accommodates the sensor pad (601) in a state of the peelable film (670) stuck thereto.
14. A leak detection system includes
    a sensor device (550) for detecting that a chemical liquid that is to be injected into a blood vessel of a patient has leaked out of the blood vessel,
    a control circuit that carries out a predetermined arithmetic processing based on a signal from the sensor device, and
    a sensor pad kit described above.

(Note B)

The present application, moreover, discloses the following invention:
1. A sensor pad kit includes
    a sensor pad (701) which is flexible, and one surface thereof is adhesive, having a sensor holding portion (702*a*) on which a sensor device (550) is to be installed, and has at least two extended portions (718) extending toward an outer side from the sensor holding portion in a plan view,
a fixing member (775) which fixes the sensor device (550) to the sensor holding portion, and
a peelable film (771).

(Meaning of Terms)

'Adhesive' means having an adhesive property which may be realized by a member (such as a gel pad) forming a sensor pad having adhesive property, or may be realized by sticking a member such as a double-stick tape on one surface of the gel pad (or a predetermined elastic member in the form of a sheet).

'Fixing member' may be an adhesive sheet such as the double-stick tap as follows, and is not necessarily limited to a member which fixes a device by using the adhesive property. It may be a member which fixes a device by mechanical engagement.

2. The sensor pad kit, wherein the number of extended portions (718) is four.
3. The sensor pad kit, wherein the extended portions (718) are at mutually equal intervals and are extended radially.
4. The sensor pad kit, wherein a shape at a tip portion of at least one extended portion (718) is a substantially circular-arc shape.
5. The sensor pad kit, wherein the sensor holding portion (720*a*) is configured such that a sensor surface of the sensor device does not make a direct contact with the patient's body.
6. The sensor pad kit, wherein at least an area facing a light-emitting portion and a light-receiving portion of the sensor device of an area facing the sensor holding portion, has a light-transmitting property with respect to light from the sensor device and reflected light thereof.
7. The sensor pad kit, wherein an outer area of the sensor holding portion has a light-shielding property.
8. The sensor pad kit, wherein the fixing member is one of an adhesive layer, and an adhesive sheet (775) of which both surfaces are adhesive.
9. The sensor pad kit further includes an upper peelable film (780, 780') which is to be stuck to one of the adhesive layer and the adhesive sheet.
10. The sensor pad kit, wherein a guide line which guides a position corresponding to a distance between a predetermined reference position of an injection needle and a tip of the injection needle is displayed on an upper surface of the sensor pad.
11. The sensor pad kit, wherein the guide line has a circular-arc shape.
12. The sensor pad kit, wherein the sensor pad includes a sheet substrate (1702) and an adhesive layer (1703) stacked on a back surface thereof.
13. The sensor pad kit, wherein a portion of the extended portion of the sensor pad is provided with a non-adhesive portion (1702*t*) with no adhesive layer (1703) formed on the back surface of the sheet substrate.
14. The sensor pad kit, wherein there are at least two extended portions provided with the non-adhesive portion (1702*t*).
15. The sensor pad kit, wherein the non-adhesive portion is formed at a tip portion of the extended portion.
16. The sensor pad kit further includes
a packaging bag which accommodates the sensor pad.
17. A leak detection system includes
a sensor device configured to detect whether a chemical liquid to be injected into a blood vessel of a patient has leaked out of the blood vessel,
a control circuit that carries out a predetermined arithmetic processing based on a signal from the sensor device, and
a sensor pad kit described above.
18. The leak detection system, wherein the leak detection system detects at least a contrast medium as the chemical liquid.
19. A chemical liquid injection system includes
the leak detection system, and
a chemical liquid injection apparatus which injects at least a contrast medium as a chemical liquid.
20. The chemical liquid injection system, wherein
the chemical liquid injection system includes an injection head which holds a syringe, and a has a piston-drive mechanism for moving a piston of the syringe back and forth, and a console which is connected by a wired or wireless connection to the injection head, as the chemical liquid injection apparatus.

Technical matter disclosed as a predetermined embodiment of the present specification can be combined with other embodiments without departing from scope of the present invention. In the 'notes' reference numerals in parentheses are only for reference, and do not limit the present invention. Moreover, even when the invention is common to a plurality of embodiments, reference numerals of a typical predetermined embodiment are indicated.

DESCRIPTION OF REFERENCE NUMERALS

100 CHEMICAL LIQUID INJECTION APPARATUS
102 CABLE
110 INJECTION HEAD
120*a* RECESS
111 MOVABLE STAND
130 PISTON-DRIVE MECHANISM
144 CONTROL SECTION
145 READER/WRITER
146 STORAGE SECTION
150 CONSOLE (INJECTION CONTROL UNIT)
151 DISPLAY UNIT
153 CONTROL SECTION
154 STORAGE SECTION
157 HAND UNIT
158 INTERFACE TERMINAL
159 OPERATION PANEL
200 SYRINGE
221 CYLINDER MEMBER
222 PISTON MEMBER
225 IC TAG
230 EXTENSION TUBE
231*a*~231*c* TUBE
300 IMAGING APPARATUS
303*a* CONTROL SECTION
300*b* IMAGING SECTION
304 BED
501 LEAK DETECTION SYSTEM
505*b* PARTITION WALL
510 SENSOR HEAD
511 LIGHT-EMITTING ELEMENT
512 LIGHT-RECEIVING ELEMENT
515 HOUSING
517 SENSOR SURFACE
517*a* CENTRAL OPENING PORTION
518 LIGHT-TRANSMITTING MEMBER
519 HOLDING MEMBER
520 SENSOR CONTROL SECTION
530 LEAK DETERMINING SECTION
550, 1550 SENSOR HEAD 555, 1555 HOUSING
556 CABLE
557 SENSOR SURFACE
600 SENSOR PAD KIT
601 SENSOR PAD
610 FLEXIBLE BASE MEMBER
610h OPENING PORTION
618 EXTENDED PORTION
620 SENSOR HOLDING PORTION
620 RECESS
621 LIGHT-SHIELDING WALL
671, 671f, 671r PEELABLE FILM
671t TAB
675 INDICATOR PORTION
673 POSITIONING RECESS
677 SENSOR-HEAD INDICATOR PORTION
678 GAUGE PORTION
679 INDICATOR PORTION
701 SENSOR PAD
702 SHEET SUBSTRATE
702a SENSOR HOLDING PORTION
703 GEL PAD
706-1 FIRST COLORED LAYER
706-2 SECOND COLORED LAYER
718 EXTENDED PORTION
718g-1, 718g-2 GUIDE LINE
775 ADHESIVE SHEET (DOUBLE-STICK TAPE, FIXING MEMBER)
771 PEELABLE FILM
771a PARTING LINE
780, 780' UPPER PEELABLE FILM
781 FIRST PORTION
781a STICKING PORTION
781b TAB
782 SECOND PORTION
782a STICKING PORTION
782b EXTENDED PORTION
782b-1, 782b-2 INDICATOR PORTION
785 SLIT
1559 FLANGE PORTION
1580 OPERATION UNIT
1585 SUBSTRATE MODULE
1702t NON-ADHESIVE PORTION
S121 ADAPTER
S122 ADAPTER
RP1, RP2 INTERSECTION POINT

The invention claimed is:

1. A sensor pad kit, comprising:
a sensor pad which is flexible, and one surface of which is adhesive, having a sensor holding portion to which a sensor device is to be attached, and at least two extended portions extending toward an outer side from the sensor holding portion in a plan view, wherein the sensor holding portion is transparent for the light from the sensor device and reflected light thereof, wherein the sensor pad has a plurality of guide indicators for different length needles on its upper surface, the guide indicator representing length of a needle so that a user can attach the sensor pad to a patient's skin after a needle has pierced the skin, and wherein the guide indicators have a circular-arc shape;
a fixing member which fixes the sensor device to the sensor holding portion; and
a peelable film which is stuck to an adhesive surface of the sensor pad.

2. The sensor pad kit according to claim 1, wherein the number of extended portions is four.

3. The sensor pad kit according to claim 1, wherein the extended portions are at mutually equal intervals and are extended radially.

4. The sensor pad kit according to claim 1, wherein a shape of a tip side of at least one extended portion is a substantially circulate-arc shape.

5. The sensor pad kit according to claim 1, wherein in the sensor holding portion is configured such that a sensor surface of the sensor device does not directly contact with a patient's body.

6. The sensor pad kit according to claim 1, wherein an outer area of the sensor holding portion has a light-shielding property.

7. The sensor pad kit according to claim 1, wherein the fixing member is one of an adhesive layer, and an adhesive sheet of which both surfaces are adhesive.

8. The sensor pad kit according to claim 7, comprising:
an upper peelable film which is to be stuck to one of the adhesive layer and the adhesive sheet.

9. The sensor pad kit according to claim 1, wherein the sensor pad includes a sheet substrate and an adhesive layer formed on a back surface thereof.

10. The sensor pad kit according to claim 9, wherein a part of the extended portion of the sensor pad is provided with a non-adhesive portion with no adhesive layer formed on the back surface of the sheet substrate.

11. The sensor pad kit according to claim 10, wherein there are at least two extended portions provided with the non-adhesive portion.

12. The sensor pad kit according to claim 10, wherein the non-adhesive portion is formed at a tip portion of the extended portion.

13. The sensor pad kit according to claim 1, further comprising:
a packaging bag which accommodates the sensor pad.

14. A leak detection system, comprising:
a sensor device configured to detect whether a chemical liquid to be injected into a blood vessel of a patient has leaked out of the blood vessel;
a control circuit that carries out a predetermined arithmetic processing based on a signal from the sensor device; and
a sensor pad kit according to claim 1.

15. The leak detection system according to claim 14, wherein the leak detection system detects at least a contrast medium as the chemical liquid.

16. A chemical liquid injection system, comprising:
a leak detection system according to claim 14; and
a chemical liquid injection apparatus which injects at least a contrast medium as a chemical liquid.

17. The chemical liquid injection system according to claim 16, wherein the chemical liquid injection system includes an injection head which holds a syringe, and has a piston-drive mechanism for moving a piston of the syringe back and forth, and a console which is connected by one of a wired connection and a wireless connection to the injection head, as the chemical liquid injection apparatus.

18. A sensor pad kit, comprising:
a flexible sensor pad with an adhesive surface, the sensor pad having a sensor holding portion to which a sensor device is to be attached and at least two extended portions extending toward an outer side from the sensor holding portion in a plan view, wherein the sensor holding portion is transparent for the light from the sensor device and reflected light thereof whereas an outer area of the sensor holding portion has light-shielding property, wherein the sensor pad has a plurality of guide indicators for different length needles on its upper surface, the guide indicator representing length of a needle so that a user can attach the sensor pad to a patient's skin after a needle pierce the skin, and wherein the guide indicators have a circular-arc shape;
a fixing member which fixes the sensor device to the sensor holding portion; and
a peelable film which is stuck to an adhesive surface of the sensor pad.

* * * * *